(12) United States Patent
Desai et al.

(10) Patent No.: US 10,791,992 B1
(45) Date of Patent: Oct. 6, 2020

(54) SYSTEM AND METHOD FOR MULTI-PARAMETER CHARACTERIZATION OF BIOLOGICAL TISSUES

(71) Applicant: UNIVERSITY OF MARYLAND, College Park, MD (US)

(72) Inventors: Jaydev P. Desai, Marietta, GA (US); Hardik Jeetendra Pandya, Bangalore (IN); Kihan Park, Atlanta, GA (US)

(73) Assignee: University of Maryland, College Park, MD (US)

( * ) Notice: Subject to any disclaimer, the term of this patent is extended or adjusted under 35 U.S.C. 154(b) by 300 days.

(21) Appl. No.: 15/631,275

(22) Filed: Jun. 23, 2017

Related U.S. Application Data

(60) Provisional application No. 62/353,921, filed on Jun. 23, 2016.

(51) Int. Cl.
*B01L 99/00* (2010.01)
*A61B 5/00* (2006.01)
*G01N 21/64* (2006.01)
*G01N 21/59* (2006.01)

(52) U.S. Cl.
CPC .............. *A61B 5/72* (2013.01); *A61B 5/68* (2013.01); *G01N 21/6458* (2013.01); *A61B 5/0062* (2013.01); *G01N 21/59* (2013.01)

(58) Field of Classification Search
CPC ... G01N 1/36; G01N 1/06; G01N 2035/00128
USPC ................................................. 422/500, 536
See application file for complete search history.

(56) References Cited

U.S. PATENT DOCUMENTS

| | | | | |
|---|---|---|---|---|
| 5,736,033 | A | * | 4/1998 | Coleman ................ B01D 21/24 210/122 |
| 2007/0191737 | A1 | * | 8/2007 | Freeman ............ A61B 5/14546 600/583 |

* cited by examiner

*Primary Examiner* — Natalia Levkovich
(74) *Attorney, Agent, or Firm* — Meunier Carlin & Curfman LLC

(57) ABSTRACT

A system for automated simultaneous measurements of multiple parameters (mechanical, electrical and/or thermal) of biological tissues includes a base platform supporting a biochip holder module with a biochip integrated therein and an indenter for nano- and micro-scale indentation of a tissue. The biochip is formed with an array of micro-sensors, for example, electromechanical micro-sensors integrated on a substrate of the biochip. A temperature microsensor maybe additionally formed, for example, on the tip of the indenter to measure thermal characteristics of the tissue specimen heated by the micro-heater fabricated on the biochip.

20 Claims, 23 Drawing Sheets

SYSTEM AND METHOD FOR MULTI-PARAMETER CHARACTERIZATION OF BIOLOGICAL TISSUES

CROSS REFERENCE TO THE RELATED APPLICATION(S)

This Utility Patent Application claims priority to, and the benefit of U.S. Provisional Patent Application No. 62/353,921, filed on Jun. 23, 2016, which is incorporated by reference herein in its entirety.

STATEMENT REGARDING FEDERAL SPONSORED RESEARCH AND DEVELOPMENT

This invention was made with Government support under R01CA161375 awarded by the NIH. The Government has certain rights in the invention.

FIELD OF THE INVENTION

The present invention is directed to bio-medical robotics, and more in particular, to Micro-Electro-Mechanical System (MEMS)-based electro-thermo-mechanical phenotyping of benign and malignant tissues.

More in particular, the present invention directs itself to a MEMS-based pathology diagnostic system, and specifically, to a portable high efficiency pathology diagnostic tool for simultaneous multi-parameter characterization of tissues under study.

The present invention further directs itself to a portable multi-parameter cancer diagnostic system capable of simultaneous measurement of multiple parameters of a tissue under study which is designed for acquiring deterministic and quantitative information on the tissue properties using a multi-functional flexible micro-sensor integrating mechanical and electrical, as well as other, micro-sensors which are arrayed on a single substrate.

The present invention pertains to design and fabrication of an array of electro-mechanical micro-sensors on a flexible substrate for diagnosis of various cancers which provides a unique opportunity for a speedy determination of a malignancy in tissues, as well as the stage of a disease progression from the onset of the disease.

The present invention is further directed to a tissue characterization system for automated pathology diagnosis using disposable single-use components (such as a multi-functional biochip sensor, and a biochip holding module), as well as a base platform (which may be used in numerous studies), to achieve a controllable reliable mechanical and electrical contact between the biochip (or MEMS) and the tissue under study. Additionally, an external electronic circuitry for data acquisition and analysis is provided, as well as a data output unit (such as, for example, a digital display, printer, plotter, etc.) for presenting the results of measurements and processing to a system user.

The present invention is also directed to a portable cancer diagnostic tool integrated with a multi-functional sensing biochip for automated cancer diagnostic studies, where, during a measurement routine, the biochip is automatically brought into controllable contact with the tissue under study for simultaneous measurement of electrical, thermal, and mechanical properties of the tissue, as well as the coupling factor between these and other various parameters (such as optical and chemical properties). Signals corresponding to the simultaneously measured electrical, mechanical, and thermal properties of the tissue are transmitted (wirelessly or via a cable) to a remote data processing sub-system, or an external mobile device (such as, a smartphone, a mobile phone, iPhone, etc.) for data analysis, diagnosis making, and displaying diagnostic messages.

Moreover, the present invention is directed to a bio-medical robotic system for characterization of normal and malignant tissues which uses a base platform supporting a biochip fabricated with one or more micro-sensors operationally based on different physical principles and a micro-indentation mechanism controllably displaceable relative to the tissue to facilitate the acquisition of various (electrical, thermal, mechanical, as well as chemical, optical and other) properties of the tissue under study.

In addition, the present invention is directed to a portable hand-held multi-parameter cancer diagnostic device designed to hold tissue in contact with an integrated multi-functional sensing biochip fabricated with an array of micro-sensors on the same substrate, and using a controllably actuated micro-manipulator (for example, piezo-motor) for precise indentation (in the range of nano- and micro-Newton) of the tissue for multi-parameter characterization.

The present invention is also directed to a completely hand-held cancer diagnostic tool using the piezomotor actuation module and the disposable sensor module integrated in a single hand-held unit which is connected, either by cables or wirelessly, to an external display module, such as, for example, a screen of a phone or iPhone capable of processing the measured data to generate diagnostic messages to be displayed, through an App, on the phone or iPhone's screen.

The present invention further is directed to a process for fabrication of a flexible biochip integrated with an array of multi-functional micro-sensors which is manufactured with a conductive polymer, namely, Poly(3,4-ethylenedioxythiophene): Poly(styrenesulfonate) (PEDOT:PSS), which has a high sheet resistance, strong mechanical bending, and ease of use (which makes it a viable option for fabrication of strain gauge sensors) on a substrate formed from highly flexible Poly(dimethylsiloxane) polymer (PDMS), which can be used in rapid prototyping via soft lithography and acting as a compliant polymer having Young's moduli on the order of 1 MPa.

BACKGROUND OF THE INVENTION

The advancement of surgical procedures and surgical tools, and the need for miniaturization of diagnostic and therapeutic devices has resulted in tremendous growth in R & D on Micro-Electro-Mechanical System (MEMS) devices. MEMS devices are miniature in size and can be batch fabricated at low cost, thereby having a competitive advantage over other devices. MEMS devices, being incorporated in surgical tools, are believed to facilitate surgical procedures by providing real-time feedback, tissue density measurements, temperature, and providing high preciseness for tissue cutting and extraction, thus improving surgical outcomes.

There are, however, fabrication challenges associated with integrating the MEMS devices with electronics, signal processing, and calibration in surgical and bio-medical applications. Incorporation of MEMS devices in surgical and bio-medical applications is also challenging from standpoint of packaging design and software development.

Recently, attention has been focused on flexible (or skin-like) sensor arrays with micro-scale architectures for detection of mechanical, chemical, thermal, and optical properties of biological materials. The capability of analyzing and manipulating the biological materials at a micro-scale and nano-scale range and the possibility of incorporating them into a portable lab-on-a-chip device makes the MEMS sensors a potential candidate for diagnostic capabilities.

Each year in USA alone, a large number of cancer cases are diagnosed. The transformation from benign to cancerous state changes the morphological signatures in the tumor environment (at all length scales, such as nano-scale, micro-scale, meso-scale, and macro-scale). Mechanical and electrical phenotyping have been demonstrated as promising techniques to diagnose pathology and study the progression of cancer.

However, there are no methodologies employing flexible MEMS device for accurate simultaneous electrical and mechanical characterization of tissue which could have been being performed in a highly expedited automated manner at the nano- and micro-Newton range. Such methodology, if available, would potentially open new avenues for cancer, and other pathology diagnosis.

For the mechanical characterization of biological tissues, micro-indentation is a common technique. A device for the micro-indentation should be sensitive to measuring forces in the range of nano-to-micro-Newton.

As an example of a micro-indenter system, a piezoresistive sensor proves to be an effective tool for the study of bio-mechanical properties of tissues as it can be microfabricated in an array format and, in contrast to Atomic Force Microscopy (AFM), does not require complex electronics. Piezoresistive sensors commonly use silicon for fabrication. However, silicon is a brittle material and requires high-temperature processing for fabrication of the piezoresistive sensor.

In addition, silicon has a high Young's modulus, and thus, in order to achieve large deflections of the mechanical structures, needs to be thin which deteriorates the mechanical strength of the device.

Thus, it would be highly desirable to build a piezoresistive sensor for the tissue micro-indentation with a conductive material different than silicone, which would be more flexible yet having mechanical strength, and which would not require a high temperature fabrication process.

Overall, it would be highly desirable to provide a pathology diagnostic system which would use a flexible MEMS (biochip) device for simultaneous multi-parameter (electrical-mechanical, as well as thermal, and potentially, chemical and optical) characterization of tissues, and which would be fabricated using highly flexible and conductive polymers capable of achieving large deflections while providing high mechanical strength of the biochip in operation.

SUMMARY OF THE INVENTION

It is, therefore, an object of the present invention to provide a system and method for simultaneous multi-parameter characterization of biological tissues for an automated, accurate, high throughput and expedited detection of pathology in tissues under study, as well as the stage of the pathology progression from the onset of the disease.

It is another object of the present invention to provide a portable bio-medical robotic system using a flexible MEMS-based "lab-on-a-chip" sensor device (biochip) integrating mechanical and electrical micro-sensors, as well as means facilitating thermal measurements, on a single substrate to enable simultaneous study of electro-thermo-mechanical properties of benign and cancerous tissues under study.

It is also an object of the present invention to provide a completely hand-held cancer diagnostic tool using the piezomotor actuation module and the disposable sensor module, as well as on-board power supply, all integrated in a single hand-held unit which is connected, either by cables or wirelessly, to an external display/processor module, such as, for example, a smartphone, mobile phone, iPhone, etc., which is capable of processing the measured data and generate diagnostic messages to be displayed on the screen through an installed App.

It is a further object of the present invention to provide a portable automated system using MEMS devices for surgical and bio-medical applications, which would be capable of precise multi-parameter indentation of biological materials at micro-Newton and nano-Newton ranges which are incorporated into a portable, preferably hand-held, diagnostic tool, adapted for identification of biological tissues' pathologies, including various types of cancers.

It is an additional object of the present invention to provide a method for fabrication of a portable multi-parameter cancer diagnostic system using a flexible array of electro-mechanical micro-sensors and a micro-heater formed on a single substrate for simultaneous electrical, mechanical, and thermal characterization of tissue under study for pathology diagnosis and characterization of the disease progression.

Moreover, it is an object of the present invention to provide a low-cost method for fabrication of a flexible biochip integrated with an array of multi-functional micro-sensors using polymers exhibiting high flexibility and conductivity for improved mechanical strength and preciseness of the diagnostic process.

It is still a further object of the present invention to provide a portable (preferably, hand-held) cancer diagnostic tool using a disposable sensing module integrated with a multi-parameter sensing biochip, which contemplates a combination of micro-fabrication technology, reliable packaging, and simultaneous multi-parameter tissue characterization, and which uses press fit contacts to the sensors of the biochip for measuring electro-thermo-mechanical properties of the tissue, thus overcoming the challenges of soldering or wire bonding at a small scale, and promoting the portability of the device.

It is a further object of the present invention to provide a flexible MEMS-based electro-thermo-mechanical sensor array for cancer diagnosis capable of simultaneous detection of electro-mechanical and thermal properties of tissue under study at micro-Newton and nano-Newton scale in an expedited and high throughput manner, where the data produced by the sensors relative to the mechanical, electrical, and thermal properties of the tissue are transmitted (through a wireless and wired communication channel) to a processing system, which conditions and processes the acquired data, performs data analysis, and transmits the results of the data analysis to a data output unit (such as, for example, a digital display module, or printer, or the screen of a mobile device, such as a phone) for presentation to a user.

In addition, it is still an object of the present invention to provide a multi-parameter cancer diagnostic tool using:

(a) a disposable biochip holder module integrated with a biochip fabricated with a number of micro-sensors fabricated on a single biochip wafer operationally based on different physical principles for simultaneous measurement of multiple tissue parameters which can provide a deterministic and quantitative information of the tissue characteristics;

(b) nano- and micro-scale actuators for controllable displacement of the tissue under study in a desired contact with the biochip and applying a controllable pressure force onto the tissue specimen, where the disposable biochip holder module and the micro-actuators may be incorporated in a tool housing for implementation as a hand-held tool;

(c) a mechanism for interfacing with a user of the system, including a control panel, and LCD display, as well as a keyboard, computer, printer, plotter, etc., external, but operatively coupled to the hand-held tool; and (d) an electronics box operatively coupled to the hand-held module, as well as to the control panel and the display module (wirelessly or through cables) for processing of the acquired measurements and diagnosis. The electronic box may also contain a power source coupled to the hand-held device for powering the operation.

In one aspect, the present invention constitutes a flexible MEMS-based portable cancer diagnostic device which includes:

a biochip holder module configured with a tissue sample receiving chamber, a biochip configured with an array of multi-functional micro-sensors integrated therewith, and disposed in the biochip holder modules, and a micro-indentation mechanism operatively coupled to a tissue sample received within a tissue sample receiving chamber of the biochip holder module. The micro-indentation mechanism is configured to controllably apply a predetermined pressure to the tissue sample and to establish contiguous contact between the biochip and the tissue sample during a measurement routine. During the measurement routine, the array of the multi-functional micro-sensors integrated with the biochip produces multi-parameter measurement signals characterizing properties of the tissue sample sandwiched between the biochip and the micro-implementation mechanism.

The subject system further includes a processor sub-system operatively coupled to the biochip and configured to process the multi-parameter measurement signals received therefrom for the tissue sample diagnostics.

The array of the micro-sensors integrated with the biochip includes micro-sensors capable of measuring electrical and/or mechanical properties of the tissue sample. The biochip further includes a micro-heater integrated therewith. The micro-indentation mechanism further includes a temperature micro-sensor configured to measure (during the measurement routine) thermal properties of the tissue sample affected by thermal radiation emanating from the micro-heater formed on the biochip.

The biochip further includes:

a flexible substrate formed from (Poly(dimethylsiloxane) polymer (PDMS), an array of contact pads and an array of connectors micro-fabricated on the flexible substrate of the biochip and extending in a predetermined manner between the micro-sensors and the contact pads.

Preferably, the mechanical micro-sensors include an array of strain gauges formed from a patterned layer of Poly(3,4-ethylenedioxythiophene): Poly(styrenesulfonate) polymer (PEDOT:PSS). The electrical micro-sensors include an array of pillars formed from a patterned layer of a dielectric material (for example, a photoresist). Each pillar is disposed atop a respective one of the strain gauges and has a metal film deposited on an upper surface.

The biochip further includes a metal pad integrated therewith. The metal pad serves as a bottom electrode for the electrical measurements. Each pillar is formed with a bottom thereof in electrical contact with the metal pad.

The micro-indentation mechanism is configured with a top electrode. The bottom and top electrodes form an electrical connection through the tissue sample sandwiched therebetween and in contiguous contact therewith during the measurement routine.

Preferably, the micro-indentation mechanism includes a micro-manipulator in operative coupling to the controller unit and an indenter coupled, at one end thereof, to the micro-manipulator for reciprocative displacement of a second end of the indenter relative to the tissue sample and the biochip. The top electrode and the temperature micro-sensor are formed at the second end of the indenter. The micro-manipulator, under control of the controller unit, applies a controlled pressure onto the tissue sample and determines a contact point between the second end of the indenter and the tissue sample.

The micro-manipulator displaces the indenter to press the tissue sample onto the tops of the pillars to transfer the pressure to the array of the strain gauges disposed under the array of the pillars. Responsive to the pressure applied thereto, the strain gauges produce an output signal corresponding to an elasticity of the tissue sample.

During the measurement routine, the micro-manipulator displaces the top electrode to establish contiguous contact of the top and bottom electrodes with the tissue sample sandwiched therebetween. When current passes between the top and bottom electrodes, the biochip produces an electric output signal which depends on the electrical properties of the tissue sample. The electrical properties of the tissue sample may include a resistance and/or an electrical impedance (such as inductance and/or capacitance) of the tissue sample.

The biochip holder module is configured with a holder body which includes a bottom portion, a middle portion, and a top portion, each connectable each to the other in a predetermined alignment along the longitudinal axis of the holder body. The biochip is positioned between the bottom and middle portions of the holder body.

A PCB (Printed Circuit Board) module is positioned between the middle and top portions of the holder body. The PCB module is configured with an array of electrical connectors (pins), each electrical connector extending towards the biochip through a respective micro-channel micro-fabricated through the middle portion of the holder body to be disposed in operative electrical alignment with a respective one of the micro-sensors (specifically, in contact with contact pads) integrated on said biochip.

A signal transmission unit is operatively coupled to the PCB. The signal transmission unit has an array of output terminals, each output terminal being in a press-fitted electrical connection with a respective one of the electrical connectors formed on the PCB module. The signal transmission unit is configured for transmission of data corresponding to the measured multi-parameter signals to the processor sub-system via a signal transmission channel operatively coupling the PCB to the processor sub-system. The signal transmission channel may be a wireless transmission channel or a cable-based transmission channel. For the wireless transmission channel, each of the signals transmission unit and the processor sub-system further includes a transceiver module.

The top portion of the biochip holder module includes an opening for receiving the tissue sample. The tissue sample receiving chamber configured in the holder body is disposed, at a top end thereof, in contact with the opening, and, at a bottom end thereof, in connection with the biochip. During operation of the subject system, the indenter is brought in alignment with the opening during the measurement routine.

The subject system further includes a base platform configured to support the biochip holder module and the micro-indentation mechanism in a predetermined positional relationship therebetween.

A digital display is operatively coupled to the biochip to receive and display data corresponding to the measured multi-parameter signals. A control panel is operatively coupled to the digital display, the biochip, the micro-indentation mechanism, and the processor sub-system. The control panel serves as an interface with a user.

The processor sub-system further includes a DAQ card for acquisition of the measured data, a processing unit for analysis of the measured data and diagnosis making, a memory unit for the measured data storing, and a software unit underlying the automated operation of the subject portable multi-parameter cancer diagnostic system and supporting the measurement routine.

The subject portable multi-parameter cancer diagnostic system is also envisioned for use in hand-held implementation.

The subject hand-held cancer diagnostic tool includes a hand-held module having a housing incorporating the base platform with the micro-indentation mechanism supported thereon and the biochip holder module removably installed on the base platform.

The hand-held device is operatively coupled to the digital display, the control panel, the processing sub-system, and a measuring routine actuating mechanism.

Upon activation of the actuating mechanism by a user, the micro-controller, under control of the processor sub-system, initiates (or aborts) the measurement routine, and the processing sub-system responses accordingly by initiating (or aborting) the data analysis routine.

In another aspect, the present invention constitutes a method for manufacturing of a portable multi-parameter cancer diagnostic system. The subject method comprises the following steps:
fabricating a biochip with an array of multi-functional micro-sensors integrated therewith,
configuring the array of the multi-functional micro-sensors to simultaneously produce multi-parameter measurement signals characterizing properties of the tissue sample,
configuring a biochip holding module configuration with a tissue sample receiving chamber, and integrating the biochip in the biochip holder module in contact with a bottom end of the tissue sample receiving chamber,
configuring a micro-indentation mechanism for controllably applying pressure to the tissue sample and positioning the micro-indentation mechanism in predetermined positional relationship with a tissue sample received within the tissue sample receiving chamber of the biochip holding module.

The subject method further assumes the steps of:
forming an actuator mechanism operatively coupled to the micro-indentation mechanism and the biochip and configured to actuate a measurement routine,
configuring and operatively coupling a processor sub-system to the biochip to process the multi-parameter measurement signals received therefrom for diagnostic purposes.

The method further continues via the steps of:
fabricating a micro-heater integrated with the biochip, and
fabricating a temperature micro-sensor on the micro-indentation mechanism, where the temperature micro-sensor is configured to measure thermal properties of the tissue sample heated by the micro-heater.

The subject method further includes the steps of:
fabricating a flexible substrate from Poly(dimethylsiloxane) polymer (PDMS),
fabricating an array of contact pads of the biochip substrate, forming the mechanical micro-sensors as an array of strain gauges formed from a patterned layer of Poly(3,4-ethylenedioxythiophene): Poly(styrenesulfonate) polymer (PEDOT:PSS),
forming the electrical micro-sensors as an array of pillars formed from a patterned layer of a photoresist (SU-8), with each pillar having a height of approximately 50 µm and a diameter of approximately 30 µm,
coating tops of the pillars with a metal film, and
forming an array of electrical connectors on the flexible substrate of the biochip between the micro-sensors and the contact pads.

The method continues by:
forming a metal pad integrated with the biochip for serving as a bottom electrode for the electrical measurements, where the pillars are formed with a bottom thereof in electrical connection with the metal pad,
forming a top electrode on the micro-indentation mechanism, where the bottom and top electrodes form an electrical connection through the tissue sample sandwiched therebetween and in contact therewith.

The measurement routine is further supported in the subject method by fabricating the micro-indentation mechanism, a micro-manipulator, and an indenter coupled, at one end to the micro-manipulator for reciprocative displacement of a second end of the indenter relative to the biochip. The top electrode and the temperature micro-sensor are formed at the second end of the indenter. The subject method assumes the step of configuring the micro-manipulator to control a distance between the second end of the indenter and the biochip for applying a pressure force onto the tissue sample in a controlled manner and for determining a contact point between the second end of the indenter and the tissue sample.

The micro-manipulator is further configured to displace, upon actuation of the actuator mechanism, the indenter to press the tissue sample onto the pillars to transfer the pressure to the array of strain gauges, which are configured in the subject method to produce, responsive to the pressure force applied thereto, an output signal corresponding to an elasticity of the tissue sample.

The subject method further assumes the step of configuring the biochip to produce an electric output signal which depends on the electrical properties of the tissue sample when the top electrode and the bottom electrode are positioned in contiguous contact with the tissue sample sandwiched therebetween, and current passes between the top and bottom electrodes.

These and other objects of the present invention will be apparent from reading the Detailed Description of the preferred embodiment(s) of the present invention in conjunction with the Patent Drawings accompanying the description.

BRIEF DESCRIPTION OF THE DRAWINGS

FIG. 8A illustrates the micro-heater, FIG. 8B depicts Cr/Au interdigitated electrodes over the micro-heater, FIG. 8C shows the sensing layer of the biochip, FIG. 8D is representative of the gold-coated SU-8 pillars over the Cr/Au electrodes over silicon dioxide layer over the sensing layer, and FIG. 8E depicts a backside of the silicon diaphragm;

DESCRIPTION OF THE PREFERRED EMBODIMENT(S)

Figure 1A:
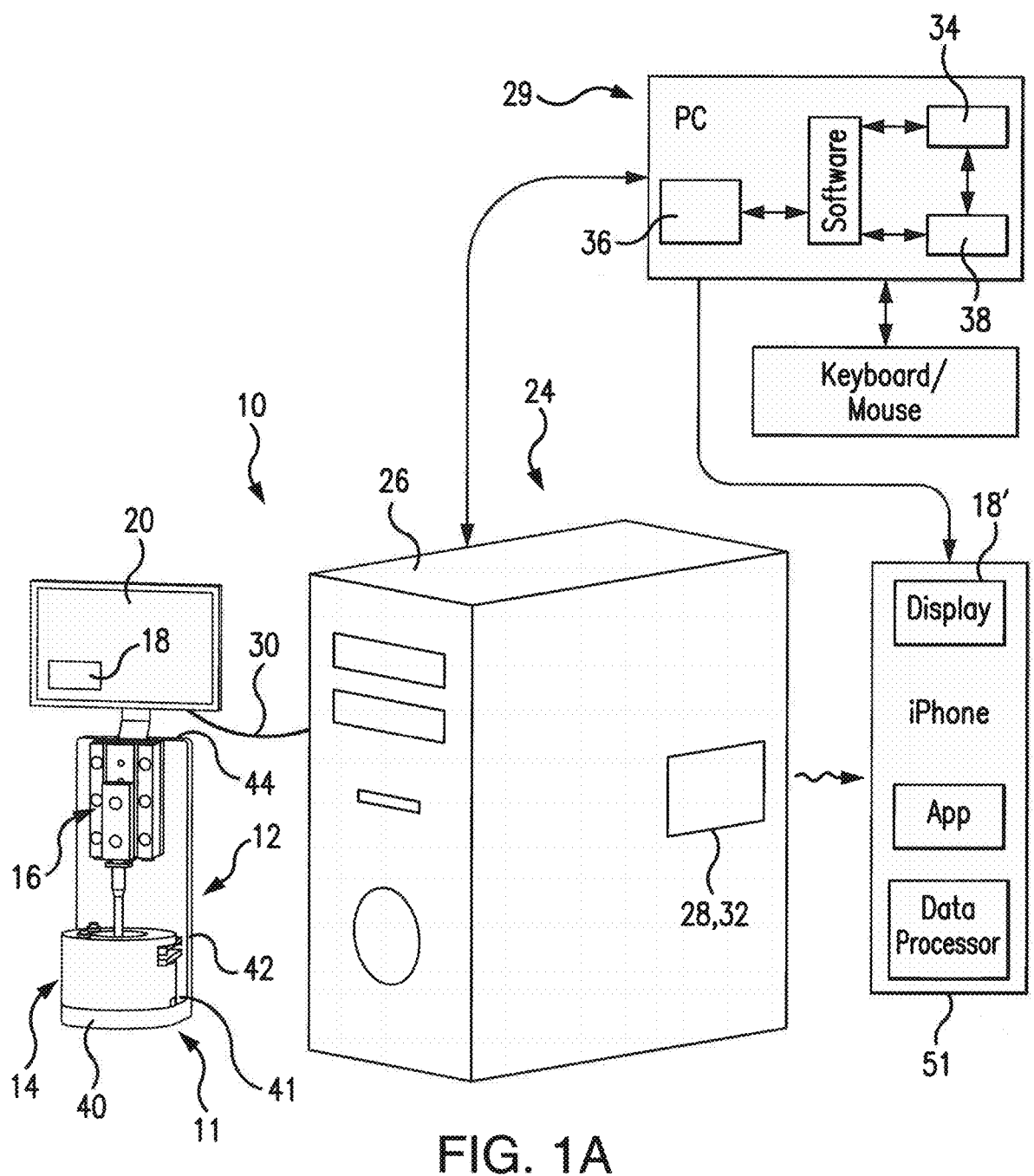
FIG. 1A is a schematic diagram of the subject portable cancer diagnosis system.

The changes in the mechanical, electrical, thermal and other properties of tissues can be used as an indicator to identify and characterize various types of pathology, including cancers, in a tissue under study.

The present system is designed for simultaneous measurement of a biological tissue's multiple parameters which can provide deterministic and quantitative information of the tissue under study. The parameters may include, but are not limited to, mechanical, electrical, and thermal, as well as chemical and/or optical, characteristics of the tissue under study. These characteristics may be indicative of a pathological process in the tissue under study and may provide characterization of the tissue from the onset through a disease progression.

The present system uses a flexible biochip, also referred to herein intermittently as micro-electro-mechanical systems (MEMS)-based device, which provides a unique opportunity for automatic accurate expedited characterization of normal and malignant tissues.

The present system uses the flexible biochip integrating array of mechanical and the electrical micro-sensors on the same platform, to enable the study of the change in electro-mechanical properties of the benign and cancerous breast tissues. In addition, the present system is capable of measuring the thermal characteristics of the tissue under study by providing a micro-heater integrated on the same substrate with the electro-mechanical micro-sensors of the biochip and a mechanism for measuring the temperature of the tissue under study which is heated by the micro-heater integrated on the biochip.

Micro-indentation technique (which permits nano- and micro-Newton indentation) may be used in the present system to characterize the mechanical properties of the tissue under study.

The biochip is integrated with conducting structures to study the electrical properties of the tissue. Through electro-mechanical and thermal characterization studies using the present MEMS-based sensors, the accuracy of the present system has been measured and the difference between benign and cancer tissue specimens has been ascertained.

Referring to FIGS. 1A-1B, 2A-2C, 3A, 3B, and 4, the automated portable MEMS-based system 10 for characterization of benign and cancerous tissues for automated simultaneous multi-parameters measurements includes a portable module 11 which is configured with a base platform 12 usable in numerous studies (meaning, it does not need to be disposable). The base platform 12 is designed to support a disposable biochip holder module 14 (which is a single-study element of the subject system). The biochip holder module 14 is removably attached to the base platform 12 during the measurement routine. In addition, the base platform 12 serves as a supporting structure for the micro-indentation mechanism 16 (detailed in further paragraphs).

In an embodiment shown in FIG. 1A, the base platform 12 also may supports a control panel 18 and a digital display 20 thereon. The control panel 18 may be integrated with the digital display 20 for interface with a user of the subject system 10, who may input commands and instructions through the control panel 18 for the measurement routine. In addition, the user, by manipulating the control panel 18/display 20 may initiate (or abort) the automatic measurement routine at his/her discretion. For this purpose, the module 11 (or the display/control panel) may be provided with actuating indicia 48 on the screen (or a button on the portable module 11) for activation by a user.

Analyzed data and/or diagnostic messages (such as, for example, "cancerous" or "non-cancerous" tissue sample) may be displayed on the display 18 to be readily available to a physician. In one embodiment, the display 18 may be integrated with the portable cancer diagnostic tool 10.

Alternatively, an external display (such as, for example, a screen of a mobile device, such as a smartphone, a phone, an iPhone, etc.) may be used to display diagnostic messages. In this implementation, as shown in FIG. 1A, data after processing are communicated to an external mobile device 51 for presentation of results, and "cancerous" or "non-cancerous" diagnostic messages on the screen 18' embedded in the mobile device (phone, iPhone, etc.) 51. The data processing also may be performed on the mobile device 51 after the measurement results are communicated thereto. The use of the external device for data processing and display require the APP loading in the device 51.

The base platform 12 is designed to achieve a reliable mechanical and electrical contact between the biochip 22 integrated with the biochip holder module 14 and the external data collection and analysis sub-system 24.

A portion of the external data collection and analysis circuitry 24 (also shown in FIGS. 4B-4C) may be encased in an electronic box 26, which may incorporate a data acquisition unit (DAQ) 28 operatively coupled to the biochip 22 through a signal transmission channel 30. The signal transmission channel 30 may be wireless or use cables for bi-direction transmission of signals between the data acquisition system 28 and the biochip 22.

The electronic box 26 also may contain a power source 32 coupled to the elements in the portable module 11, as well as to the digital display 20 and control panel 18, to power the operation of the subject system.

The subject external data collection and analysis circuitry 24 further includes a computer (PC) 29 coupled to the electronics incorporated in the electronic box 26. The computer 29 constitutes a processor sub-system and operates using memory 34 for storing results of measurements as well as results of data analysis, a processor unit 36 analyzes the data in accordance with specific protocol. A controller unit 38 is configured to control the operation of the micro-indentation mechanism 16 and the automatic operation of the entire system 10 based on software underlying the operation of the subject system.

The data acquisition system 28 may be based on a DAQ card which collects the data and provides the interface mechanism between the data corresponding to the measured physical property (electrical, mechanical, and thermal properties) and the processor/controller unit 36/38. The data acquisition system 28 performs signal conditioning to convert the signals received from the biochip 22 into signals suitable for the DAQ hardware and may use DAQ device drivers which are needed in order for the DAQ hardware to operate with the processor sub-system 29.

Specialized DAQ software may be used with DAQ hardware in the present system. The software tools used in the present system may be LabChart, MIDAS, or other programming environments.

The base platform 12 may be built with a platform support 40, which is contoured to support the disposable biochip holder module 14 and to vertically position the portable module 11 on a horizontal surface.

A module wall 42 extends in an angled (preferably, orthogonal) relationship with the platform support 40. The module wall 42 provides a support for the micro-indentation mechanism 16 for vertical linear displacement relative to the biochip holder module 14 in a controlled manner as will be detailed in further paragraphs.

The upper edge 44 of the module wall 42, as shown in FIG. 1A, may support the control panel 18/digital display 20 to interface with a user 50 of the system.

Figure 1B:
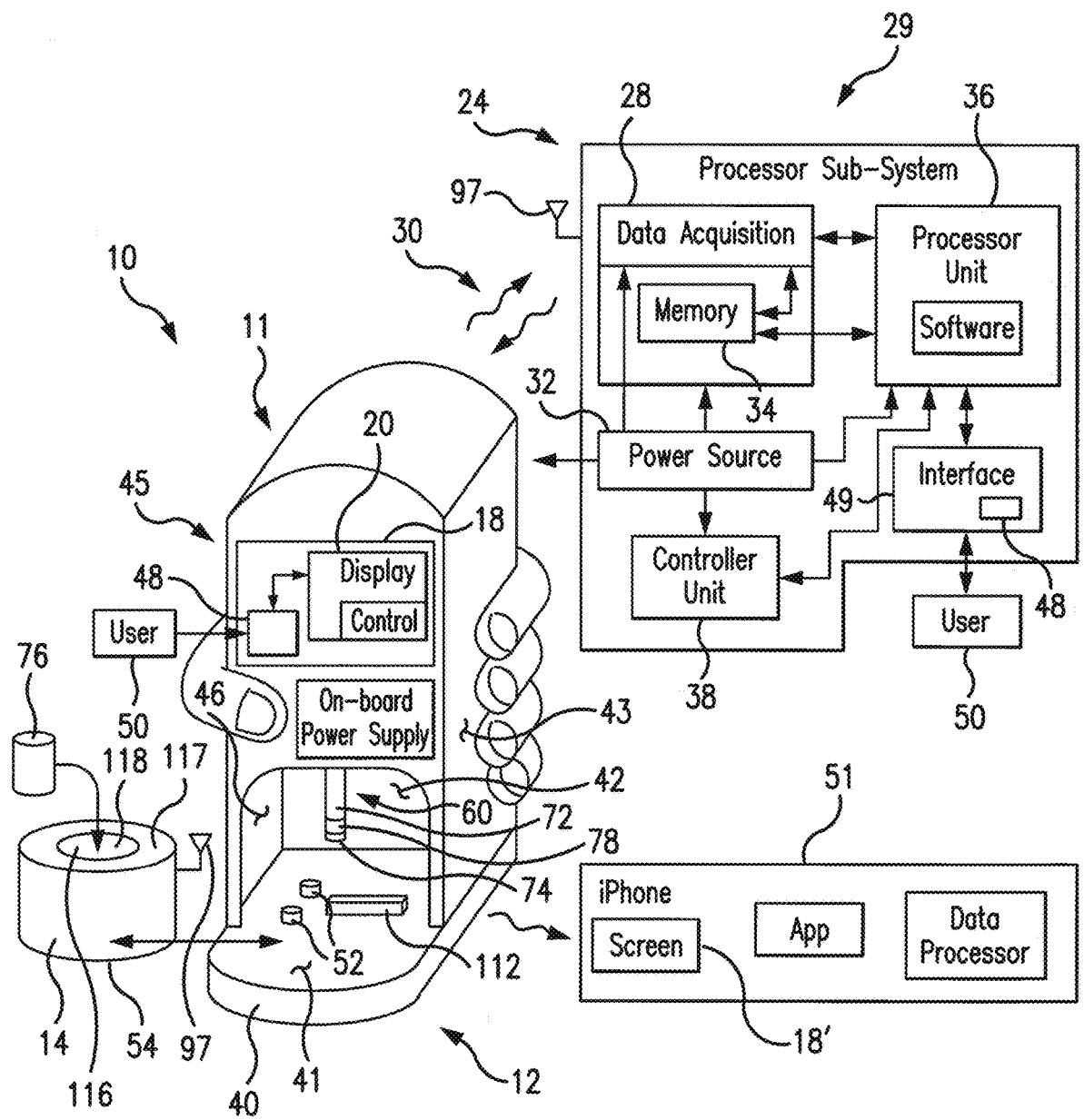
FIG. 1B is a schematic diagram of the subject portable cancer diagnostic system in a hand-held implementation.

The portable module 11 of the overall system 10 can be configured as a stationary unit (shown in FIG. 1A) or a hand-held device (shown in FIG. 1B). In the hand-held embodiment, the base platform 12 and the micro-indentation mechanism 16 attached thereto may be encased in a housing 43 to form a hand-held module 45.

The display 20 and a control panel 18 in this embodiment may be embedded in the hand-held module 45, or may be external thereto to constitute an external interface sub-system which communicates with the hand-held module 45 via a wire or wirelessly for a bi-directional signal transmission therebetween.

The completely hand-held cancer diagnostic tool (shown schematically in FIG. 1B) may use a piezomotor actuation module and the disposable biochip holder module 14, as well as on-board power supply, all integrated in the single hand-held module 45.

Alternatively, an external mobile device (such as a smartphone, a phone, iPhone, etc.) 51 may be used in wireless communication with the hand-held module 45 to receive measured data therefrom for processing the received data (on the mobile device itself), generating diagnostic messages, and displaying the results of computation on the screen 18' (App is installed in the mobile device 51 for supporting these functions of the mobile device). In this manner, the diagnostic messages reflecting the results of the study ("cancerous" or "non-cancerous" tissue sample) are readily available to a physician in an expedited fashion.

The housing 43 may have an opening 46 through which the disposable biochip holder module 14 can be installed into (or removed from) the base platform 12 in the housing 43.

The actuating indicia 48 may be provided on the control panel 18/display 20 for being manipulated by a user 50. The actuating indicia 48 alternatively may be provided at the interface 49 of the computer 29.

The actuating indicia 48 can serve the purpose of initiating the measurements for automated measurement routines as prescribed by a software underlying operation of the controller unit 38 in communication with the control panel 18. The actuating indicia 48 (or any other trigger mechanism, such as for example, a button on the portable module) may also serve the purpose of aborting the measurement routine.

As shown in FIGS. 1A-1B, 3A-3B, and 4A, the micro-indentation mechanism 16 is configured with an indenter 60, attached to a micro-manipulator 62 which provides vertical linear displacement of the indenter 60 with regard to the biochip 22. The micro-manipulator 62 is actuated by the motors 64, the operation is which is pre-programmably controlled by the external circuitry 24 for a fully automated routine as prescribed by the processor sub-system 29. In addition, the operation of the micro-indentation mechanism 16 may be controlled by a user through the control panel 18, when modifications (or alterations) to the automatic routine are needed for a specific measurement cycle.

For example, the indenter 60 may be installed on the base 66 which slides along the rails 68 formed in the support unit 70 attached to (or formed integrally with) the module wall 42 of the base platform 12. The displacement of the indenter 60 with regard to the module wall 42 has a travel range (for example, 21 mm) with a resolution of approximately 1 nm.

Figure 3A:
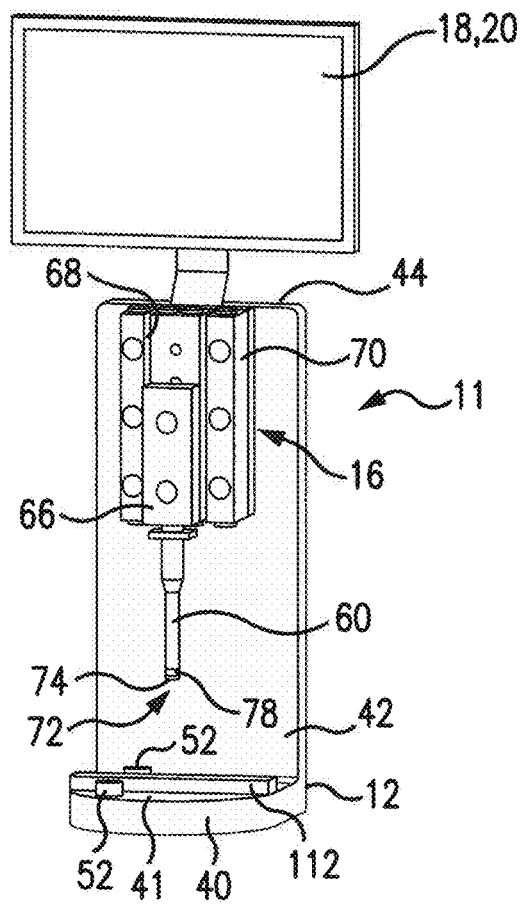
FIG. 3A is a schematic representation of the base platform, supporting the micro-indentation mechanism, display, and control interface used in the subject system.

Although any type of a micro-actuator can be used in the subject system as part of the micro-indentation mechanism 16, as an example (but not to limit the scope of protection of this particular embodiment), FIG. 3A shows a piezoelectric actuator which converts electrical energy into linear motion of the indenter 60 with high speed force and virtually unlimited resolution. The principles of the operation of piezo-electric actuators are known to those skilled in the art and are not detailed herein.

Figure 3B:
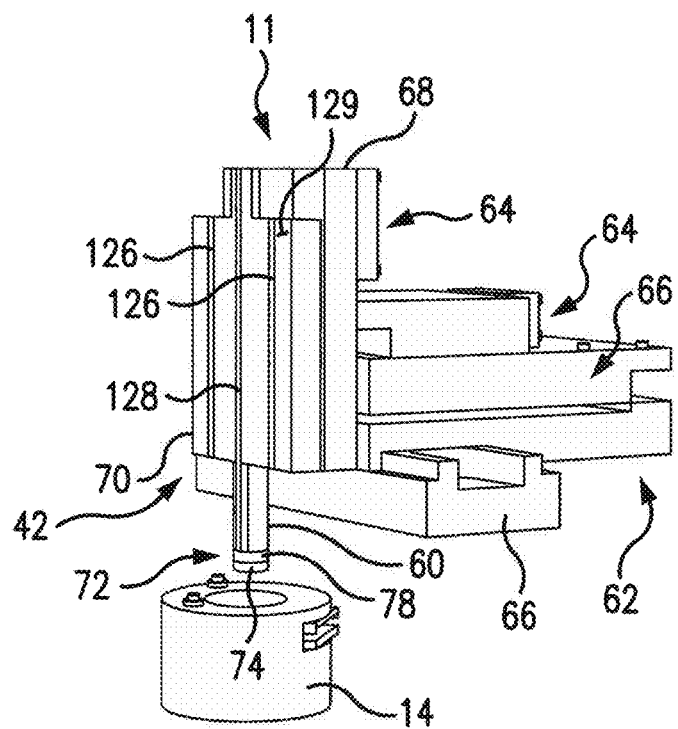
FIG. 3B is a schematic representation of the subject diagnostic system detailing electrodes for the temperature sensor and electrical contact to the tissue, as well as micromanipulator of the micro-indentation mechanism.
Figure 4A:
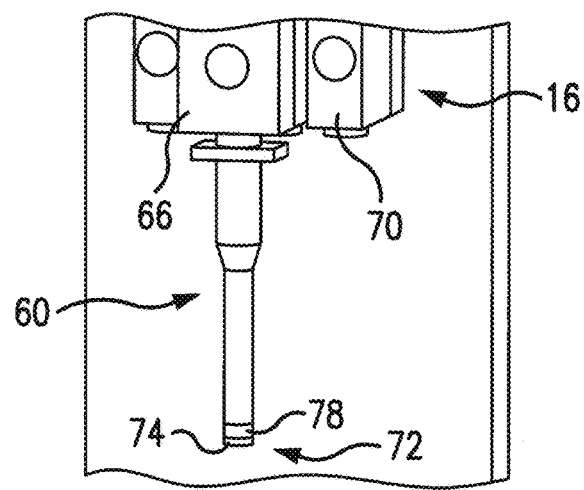
FIG. 4A is a magnified view of the indenter with a top electrode (E1) and a thermistor formed at the tip thereof.

As shown in FIGS. 3A-3B and 4A, the tip 72 of the indenter 60 is coated with a metal film acting as a top electrode 74 (E1) to be used in electrical characterization and for contact point determination between the indenter 60 and the tissue sample 76. During the measurement routine, the tip 72 is inserted into the biochip holder module 14 and presses on the tissue sample to be brought in contact with the sensor array on the biochip 22, as best shown in FIGS. 4C and 12A-12C.

A temperature sensor 78 (which may be a thermistor or any other temperature sensor) is also integrated on the tip 72 of the indenter 60 to measure the thermal characteristics of the tissue sample heated by the thermal energy emanating from a micro-heater 80 formed on the biochip 22 as will be presented in future paragraphs with regard to FIGS. 8A-8H.

Figure 2A:
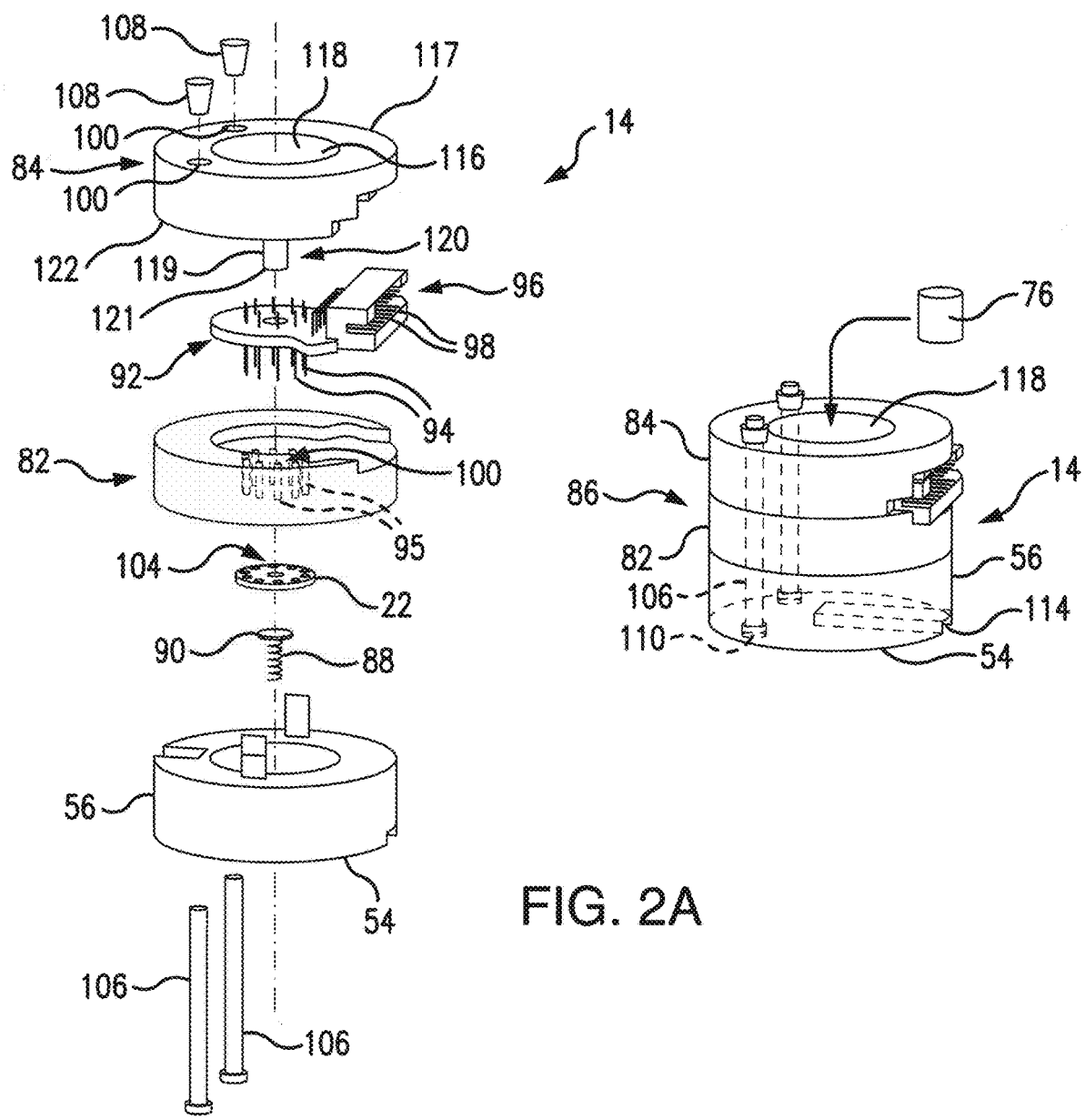
FIG. 2A is an exploded view of the disposable biochip holder module used in the subject system.
Figure 2B:
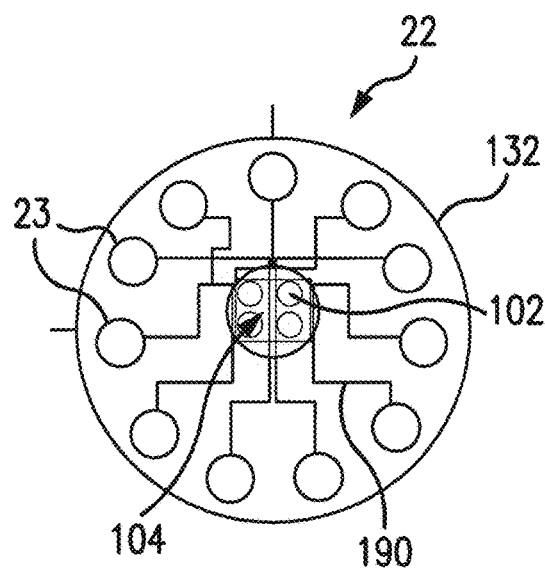
FIG. 2B is a magnified view of the subject biochip.
Figure 2C:
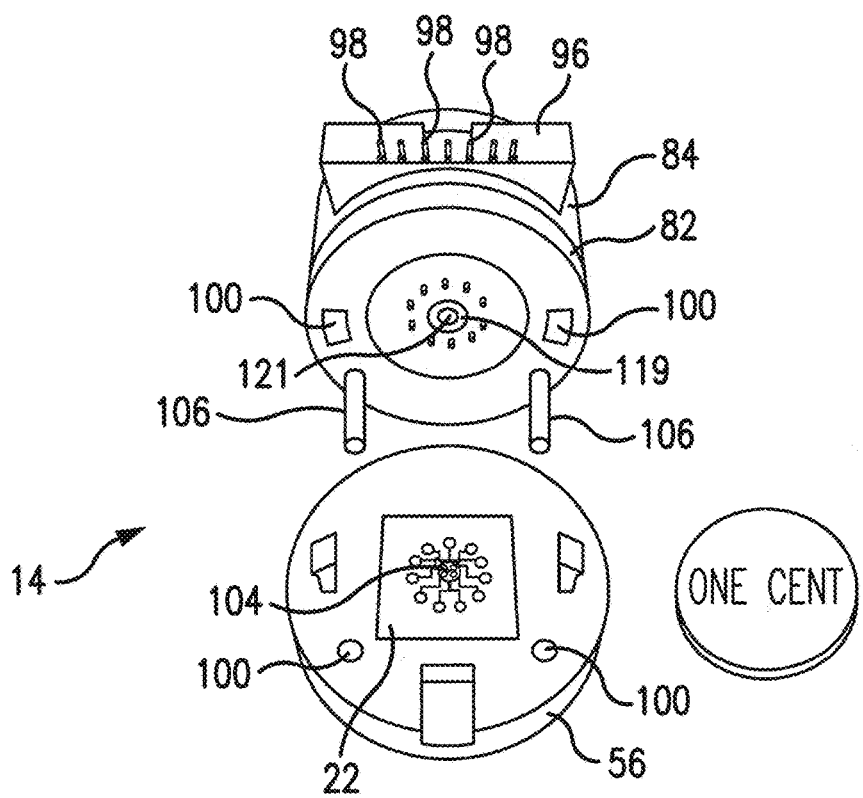
FIG. 2C depicts the biochip installed between the bottom and the middle parts of the subject biochip holder module.

Referring to FIGS. 2A-2C, the biochip holder module 14 includes a bottom portion (also referred to herein intermittently as a part) 56 having a bottom 54, a middle portion 82, and a top portion 84 which are connected each to the other along the longitudinal axis of the biochip holder module 14 to form the holder body 86. The biochip 22 is positioned between the bottom portion 56 and the middle portion 82 of the module 14 and is supported by a spring 88 and the pad 90 to cushion the motion of the biochip 22 when the tissue sample is brought into contact therewith.

A printed circuit board (PCB) 92 is installed between the middle and top parts (portions) 82, 84 of the module 14. The PCB 92 is formed with press fitted contacts 94 formed on the PCB 92 and disposed in operative contact with the micro-sensors integrated with the biochip 22 to be in precise contact with the contact pads 23 on the biochip 22. The contact pads 23 are formed on the biochip 22 in coupled relation to respective micro-sensors 102 of the array 104 thereof.

In the example shown in FIGS. 2B, 5A-5C, 8B-8D and 8F, the contact pads 23 are disposed on the periphery of the biochip's substrate and are connected to the array 104 of micro-sensors via a serpentine-like connection 190 which promotes the biochip miniaturization.

The contact pins 94 on the PCB 92, as shown in FIG. 2A, are also disposed in a circumferential fashion at the PCB periphery to align with the contact pads 23 on the biochip 22. This geometrical arrangement is also beneficial from the standpoint of avoiding interference between the contact pins 94, as well as micro-channels 95, with the tissue passing channel 119, which is preferably positioned centrally with respect to the holder body 86, as dictated by the need for alignment of the tissue sample core with the sensing portion of the biochip 22 where the array 104 of micro-sensors 102 and the micro-heater 80 are disposed.

When the indenter 60 (being controlled by the controller unit 38) presses on the tissue specimen 76, the tissue specimen is brought in contact with the biochip 22, and the contact pins 94 are brought in contact with respective contact pads 23 connected to the micro-sensors on the biochip 22.

The middle part (portion) 82 of the biochip holder module 14 is micro-fabricated with numerous micro-channels 95. The contact pins 94 are press-fitted into the micro-channels 95 and extend therethrough from the PCB 92 to the biochip 22.

A signal transmission module 96 is attached to the PCB 92 and provides an electrical coupling between respective contact pins 94 and wires 98 of the cable based transmission channel 30 for transmitting signals between the micro-sensors integrated with the biochip 22 and the DAQ/processing sub-system 28, 29.

When a wireless communication channel 30 is preferred for signal transmissions, the signal transmission module 96 can be modified to include a transceiver 97 both on the portable module 11 and the external electronics 24, 28, 29 (as best shown in FIG. 1B) for wireless communication with the data acquisition system 28, processor 36, controller unit 38, and memory 34 for data analysis, diagnosis, and for controlling the operation of the portable module 11.

Returning to FIGS. 2A and 2C, the bottom part 56, middle part 82, and top part 84 of the biochip holder module 14 may be manufactured through micro-fabrication technology, such as 3-D printing technology, with a number of passages 100, also referred to herein as alignment channels, which are disposed in precise alignment correspondence each with the other as they pass through the top, middle, and bottom parts 84, 82, 56, respectively. The alignment passages 100 serve the purpose of accurate coupling between the bottom, middle, and top parts, 56, 82, 84 of the biochip holder module 14. In order to retain the bottom, middle and top parts 56, 82, 84 of the biochip holder module 14 together during the measurements, the alignment columns 106 are inserted through respective alignment passages 100 extending through the bottom, middle and top parts 56, 82, 84 to serve as a holding mechanism for the biochip holder module 14. At the upper surface of the top part 84, the alignment columns 106 are terminated into the rubber packing members 108.

As shown in FIG. 3A, the platform support 40 has biochip holder module positioners 52 which extend from the surface 41 of the platform support 40 to be aligned with indentations 110 provided on the bottom 54 of the bottom part 56.

In addition, an aligning beam 112 is formed on the surface 41 of the platform support 40 to be aligned with a linear indentation channel 114 formed on the bottom 54 of the bottom part 56 of the biochip holder module 14.

When the biochip holder module 14 is installed on the platform support 40, it is easily oriented in a correct position through a sliding engagement of the indentation channel 114 on the bottom 54 of the bottom part 56 of the biochip holder module 14 and the aligning beam 112 on the surface 41 of the platform support 40 of the base platform 12, and secured in place through the removable coupling between the biochip holder module positioners 52 and the indentations 110, as well as between the aligning beam 112 and the linear indentation channel 114.

As shown in FIGS. 1B, 2A, 2C and 3B, the biochip holder module 14 is provided with a tissue entrance 116 formed on the top 117 of the top part 84 of the biochip holder module 14. The tissue entrance 116 has an opening 118 on the top 117 of the top part 84 and transforms into a tissue passing channel 119 which extends from the opening 118 at the top 117 to the bottom 120 of the tissue passing channel 119 terminating at the opening 121.

As best shown in FIG. 2A, the tissue passing channel 119 is micro-fabricated as a tube-like member extending from the bottom 122 of the top part 84 of the biochip holder module 14. The tube-like tissue passing channel 119 is received in a respective alignment passage 100 and extends from the top port 84 to the biochip 22 through the middle part 82.

A tissue specimen 76 is loaded into the biochip holder module 14 via the opening 118 at the top 117 of the top part 84 and subsequently passes through the tissue passage channel 119 into contact with the biochip 22 at the opening 121 when pushed down by the indenter 60.

As shown in FIGS. 2B, 5A-5C, 6A-6M, 7, 9A, 9C, 9E-9F, and 10-11, the biochip 22 is formed with the array 104 of electro-mechanical sensors 102, as well as the micro-heater 80, disposed at the central area of the biochip 22, and an array of contact pads 23 coupled to the respective micro-sensors 102 via serpentine-like conductive passes 190.

As shown in FIG. 3B, electrodes 126 extend between the temperature sensor 78 (preferably, along the back surface 129 of the module wall 42 of the base platform 12) and the control panel 18/display 20 to provide bi-directional signal transmission therebetween, as well as to power the temperature sensor from the power source 32 which may be disposed in the electronic box 26. To provide the electrical communication between the control panel 18/display 20 and the biochip 22, an electrode 128 extends along the module wall 42 to the electrode (E1) 74.

In order to facilitate in miniaturization of the subject device, the electrodes 126, 128 may be press-fitted in the channels formed at the back surface 129 of the module wall 42 of the base platform 12.

The disposable biochip 22 may have, for example, a diameter of 10 mm. The biochip 22 may be manufactured on a silicon, glass, or ceramic wafer. Each 4-inch silicon wafer can yield twelve biochips. The number of biochips fabricated per wafer can be increased by using a silicon wafer of larger diameter to increase the throughput in a single micro-fabrication batch process. Each biochip carries a number of piezoelectric micro-sensors forming a sensing layer of the biochip 22, and covering an area, for example, 2 mm.

A thin (in μm range) insulating layer of, for example, $SiO_2$ may be deposited over the micro-sensors. Other insulating materials, for example, including $Si_3N_4$ also may be used. The biochip 22 further includes a gold pad which acts as the bottom electrode (E2) in electrical characterization of the tissue.

Pillars 154 (approximately 100 μm thick) are fabricated on the top of the gold pad (E2) from a dielectric material (for example, a photoresist SU-8) and their tops are coated with a metal film 156.

For the measurements, the tissue sample 76 is placed in the cylindrical tissue passing channel 119 (via the opening 118 of the tissue entrance 116) and is pressed down onto the SU-8 pillars 154 using an indenter 60 connected to the micro-manipulator. The pillars are used to transfer a controlled force to the sensing layer of the biochip 22, as shown in FIG. 4C.

An output signal from the sensor array on the biochip 22 depends on the magnitude of the force sensed by the micro-sensors. The force applied from the indenter 60 on the tissue 76 and subsequently to the biochip 22 is a function of the elasticity of the tissue 76. Thus, the change in signal from the micro-sensors corresponds to the elasticity of the tissue.

A constant voltage may be applied between electrodes (the top electrode E1 and the bottom electrode E2). The electrical path is complete when the top electrode (E1) on the indenter 60 touches the tissue sample 76 and current passes through the top electrode (E1) to the tissue 76 and further to the bottom electrode (E2). The output signal (voltage/current) depends on the conductivity of the tissue which correspondingly depends on the type of the tissue (whether normal or cancerous). In addition to a constant voltage, a variety of alternative electrical signals of varying frequency can be passed through the tissue 76. The tissue resistance is not the only electrical parameter for characterizing the tissue electrical properties. Another important parameter of the electrical property of the tissue may be the electrical impedance of the tissue itself.

Figure 4B:
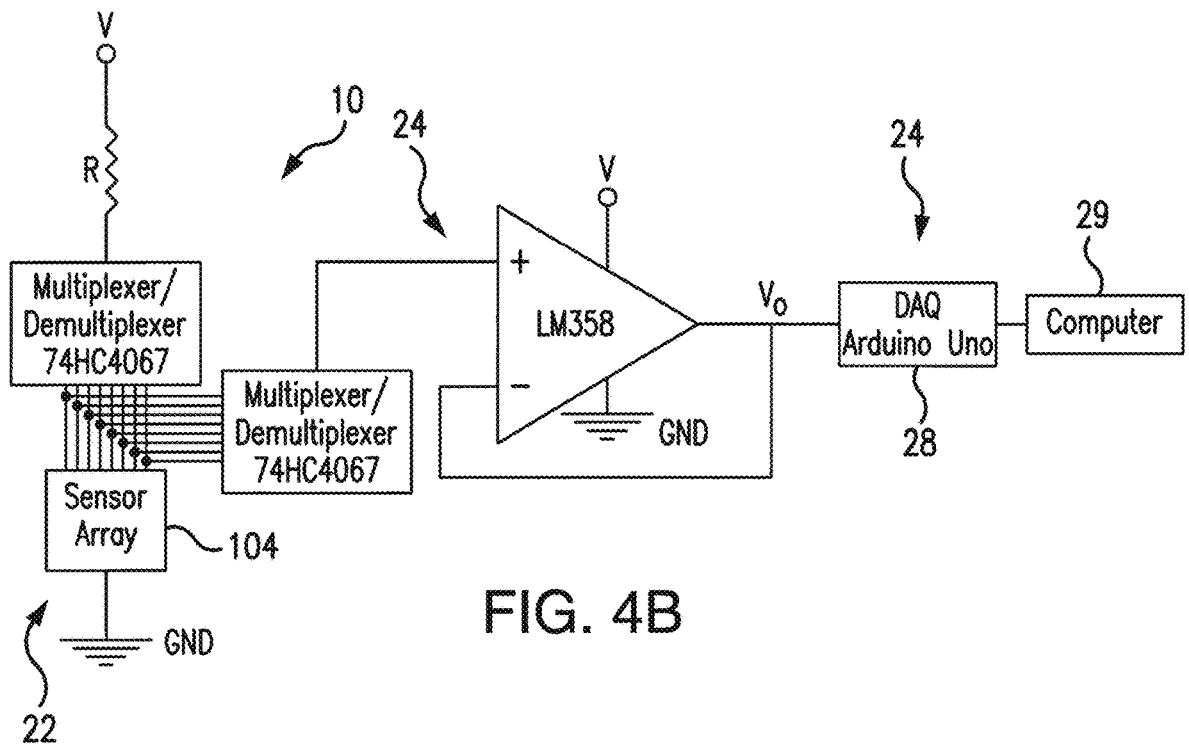
FIG. 4B is a schematic representation of the electronic circuitry for displaying voltage as a function of the indentation of the tissue sample.
Figure 4C:
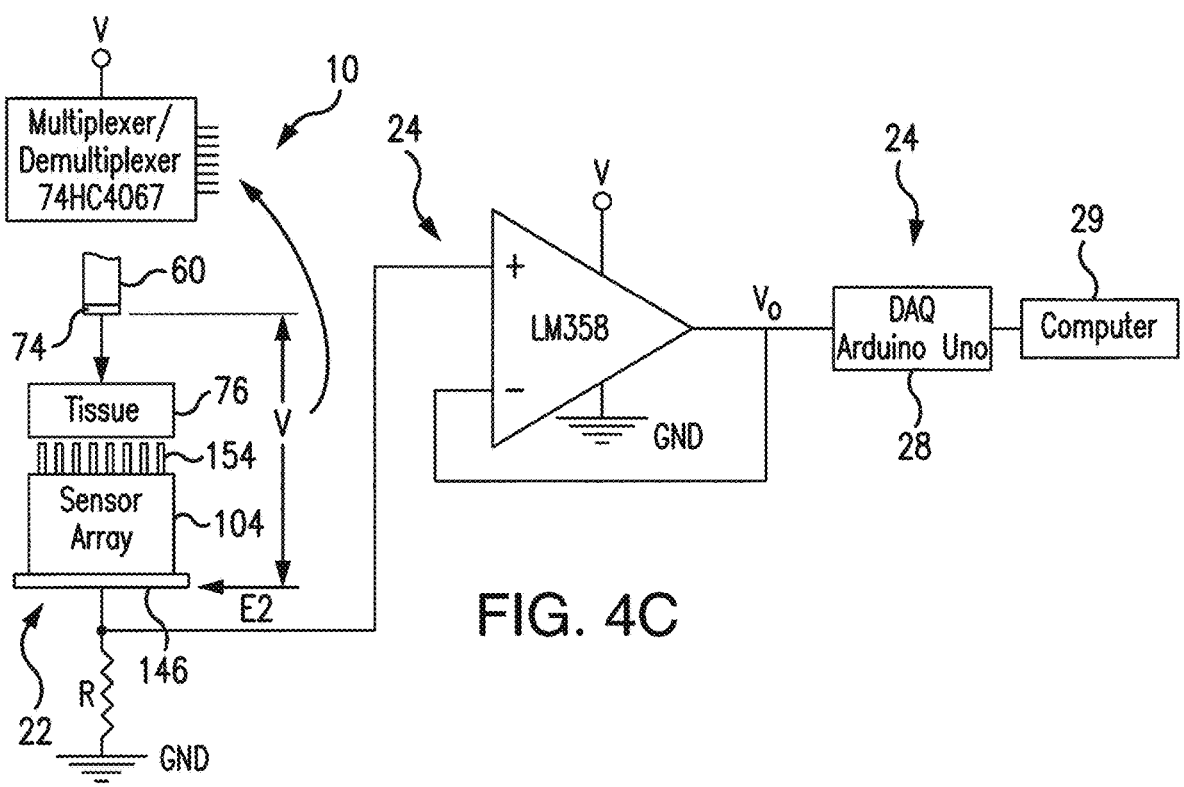
FIG. 4C is a schematic representation of the electronic circuitry for measuring electrical resistance of the tissue sample.

FIGS. 4B and 4C show schematically the electronic circuitry/processor sub-system 24, 29 for measuring voltage and electrical resistance, respectively.

For each tissue measurement, a new biochip 22 is used in order to avoid cross contamination (blood or tissue specimens left behind from previous measurements).

Referring to FIGS. 5A-5C, 6A-6M, 7, 8A-8H, 9A-9F, 10, 11, and 12A, the array 104 of electro-mechanical micro-sensors was fabricated on the PDMS substrate 134 using Poly(3,4-ethylenedioxythiohene): poly(styrenesulfonate) (PEDOT:PSS) conducting polymer atop the Poly(dimethylsiloxane) (PDMS) as the substrate material.

The conductive polymer, namely Poly(3,4-ethylenedioxythiophene): Poly(styrenesulfonate) (PEDOT:PSS) has a higher sheet resistance than other conductive polymers, strong mechanical bending capability and ease of fabrication which makes it a viable candidate for strain gauge micro-sensors fabrication.

Poly(dimethylsiloxane) (PDMS) is suitable for use in rapid prototyping with soft lithography. PDMS is a compliant polymer having moduli on the order of 1 MPa and for its qualities is explored for development of microfluidics.

In the subject system 10, the advantage of the flexibility of PDMS is combined with the high conductivity of PEDOT:PSS. The array 104 of the mechanical micro-sensors 102 has been fabricated for use in the subject system 10.

The fabrication process for manufacturing the biochip 22 is not limited to the use of the specific micro-fabrication process presented herein but can be extended to numerous other fabrication routines suitable for the manufacturing of the subject biochip 22. As presented in FIGS. 6A-6M, 7 and 8G, it is used as an example of a process to fabricate the system capable of performing the subject simultaneous electro-thermo-mechanical properties estimation of the tissue sample.

Referring to FIGS. 6A-6M, PDMS layer 134 (SYLGARD® 184 from Sigma Aldrich) was coated on a 4-inch silicon (Si) wafer 132. The sensing layers were built subsequently one on another. The Si (or, alternatively, glass or ceramics) provides structural support during the fabrication. Six mask processes were used to fabricate the flexible electro-mechanical biochip 22.

An exemplary fabrication process includes the following steps:

Step A (FIG. 6A): PDMS (140 µm thick)) layer 134 was spin coated on Si wafer 132 followed by curing at 90° C. for 12 hours in furnace;

Step B (FIG. 6B): Chrome/Gold (Cr/Au) (20 nm/500 nm) layer 136 was deposited on the top of the PDMS layer 134 through e-beam evaporation methodology.

Due to the fact that the PDMS 134 and the metal 136 deposited on PDMS may crack when a photoresist is pre-baked at 90° C., an alternative approach was also used in which a positive photoresist on the metal coated PDMS was settled down for 6 minutes followed by baking in an oven for about 1 minute at 60° C. before UV exposure. This alternative method keeps the PDMS layer 134 and the metal film 136 intact.

Step C (FIG. 6C): Cr/Au film 136 was patterned to form electrodes 138 for mechanical sensors (strain gauges) 140;

Steps D-E (FIGS. 6D-6E): PEDOT:PSS 142 was spin coated and patterned to form an array of strain gauges (0.6 µm thick) 140;

Steps F-G (FIGS. 6F-6G): Silicon dioxide (SiO$_2$) layer 144 of 0.8 µm thickness was deposited using low temperature (80° C.) plasma-enhanced chemical vapor deposition (PECVD) and patterned to open contact pads 146 for electrical connection;

Steps H-I (FIGS. 6H-6I): Cr/Au (20 nm/500 nm) layer 148 was deposited using an e-beam evaporator and patterned to form electrodes 150 for electrical sensors;

Steps J-K (FIGS. 6J-6K): Photoresist SU-8 (2025) 152 was spin coated and patterned to form pillars 154 of approximately 30 µm diameter and 50 µm height;

Step L (FIG. 6L): SU-8 pillars 154 were coated with Cr/Au film 156 using e-beam evaporation and a lift-off technique to make it electrically conductive. The angle between the wafer 132 and the gold evaporation source was maintained at 45 degrees.

Step M (FIG. 6M): The final part of the process was to release the complete biochip 22 from the Si wafer 132. The PDMS layer 134 was peeled off from the Si wafer 132. Biochip 22 was thus developed with the array 104 of micro-sensors 102 (mechanical sensors 140 and electrical sensors 154) integrated therewith.

Figure 7:
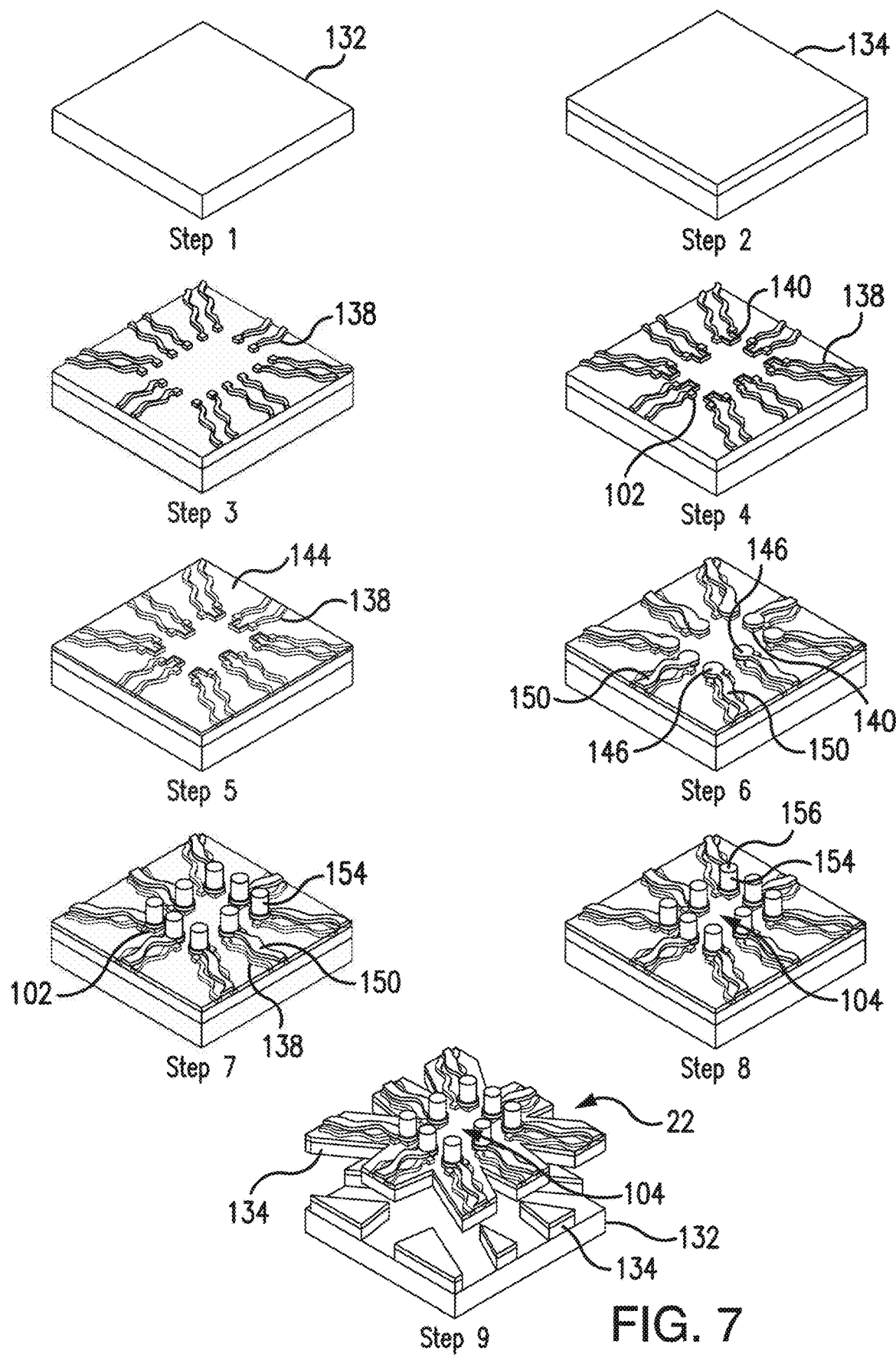
FIG. 7 is representative of the subject manufacturing process showing prospective view of the stages of the subject biochip fabrication.

Referring to FIG. 7, the flow of the subject process, which corresponds to FIGS. 6A-6M), is illustrated depicting the isometric view of the stages of the biochip 22 fabrication;

In step 1, a silicon (Si) wafer 132 was used as the base material;

In step 2, PDMS 134 was spin coated on Si wafer 132 and cured at 80° C. for about 12 hours in furnace;

In step 3, Gold (Au) 0.5 µm thickness was deposited on the PDMS layer 134 using e-beam evaporation and patterned using photolithography to form an array of electrodes 138;

In step 4, Poly(3,4-thylenedioxythiophene): Poly(styrenesulfonate) (PEDOT:PSS) conducting polymer layer (0.6 µm thick) was spin coated and patterned to form an array of strain gauges 140;

In step 5, an insulating layer 144 of silicon dioxide (SiO$_2$) of 0.8 µm thickness) was deposited using plasma-enhanced chemical vapor deposition (PECVD);

In step 6, the SiO$_2$ from areas above the strain gauges 140 was etched using reactive ion etching (RIE), and gold (0.5 µm) was deposited and patterned to form an array of electrodes 150 with a circular pad (50 µm in diameter) 146 over each strain gauge 140;

In step 7, photoresist SU-8 2025 (50 µm thick) layer was spin coated and patterned to form an array of pillars 154 (each pillar had 30 µm in diameter);

In step 8, the array of pillars 154 was coated with gold film 156 on the top and on one side of SU-8 pillar;

In step 9, the PDMS was scribed from the silicon substrate 132, and thus the biochip 22 was realized which has an array 104 of electro-mechanical micro-sensors 140, 154 integrated therewith.

Figure 12A:
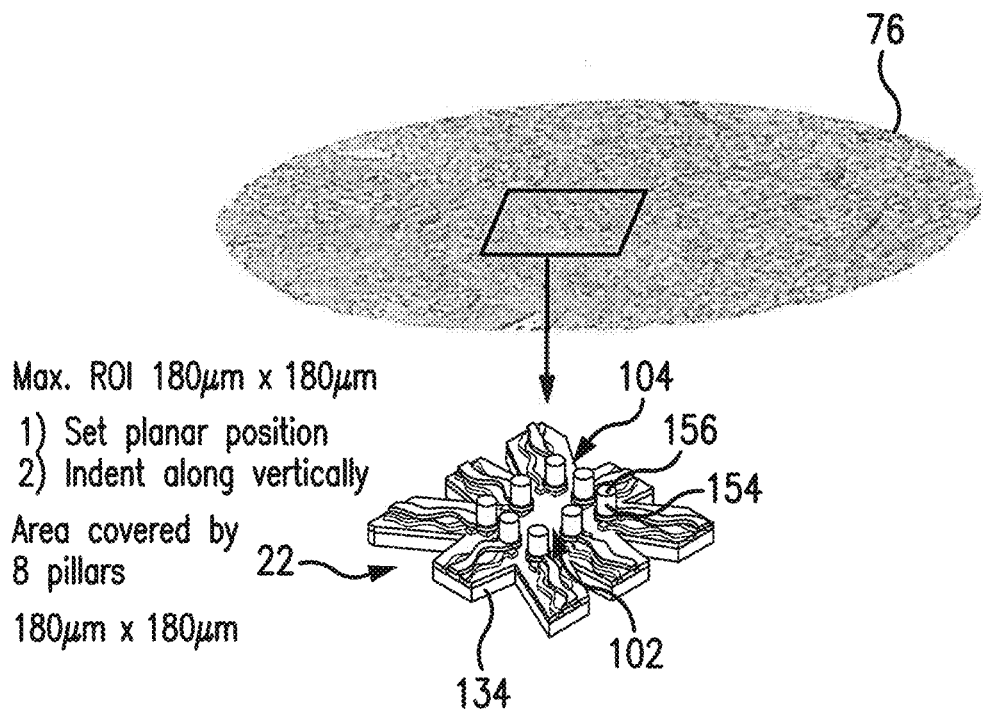
FIG. 12A is representative of the electro-mechanical measurement methodology used in the simultaneous multi-parameter measurements supported by the subject system.

As shown in FIG. 12A, in the afore-presented example, the electro-mechanical sensor array 104 covered the 180 µm×180 µm area which corresponded to the region of interest in the tissue sample core (180 µm×180 µm). The complete biochip 22 was 20 mm in diameter. The biochip 22 has to measure the changes in the benign and cancerous tissue core 76. The dimensions of the active region (sensor array) region were selected accordingly. The diameter of the biochip 22 was selected so as to facilitate the attachment of the biochip with the holder (biochip module) 14 for experimental measurements.

The diameter of the biochip 22 can be adjusted depending on the biochip holder module 14 design, but the active region dimensions are to remain corresponding to the area of interest on the tissue sample.

The biochip 22 has also been fabricated with a micro-heater 80 as shown in FIGS. 8A-8H. The biochip 22 integrated with the micro-heater 80 and the piezoresistive sensor array 104 was fabricated on an oxidized silicon substrate using a seven-mask process. The sensor array 104 covered 2000 µm×2000 µm area, while the complete biochip 22 was 10 mm in diameter.

Referring to FIGS. 8A-8E, 8F and 8G-8H, an exemplary fabrication process was as follows:

Step (i): a 4 in (100) orientation silicon (Si) wafer 132 (500 µm thick) was used as a substrate, Step (ii): µm silicon dioxide (SiO$_2$) layer 170 was grown using thermal evaporation, Step (iii): A micro-heater 80 was fabricated on the oxidized silicon substrate 132/170 by patterning sputtered deposited Nichrome (NiCr) layer (0.3 µm thick), Step (iv): SiO$_2$ (0.5 µm) layer 172 was deposited using plasma enhanced chemical vapor deposition (PECVD) over the micro-heater 80. SiO$_2$ layer 172 was etched from the contact area of the micro-heater, and the Cr/Au (0.02 µm/0.5 µm) film 174 was deposited using e-beam evaporation and patterned to form interdigitated electrodes 176;

Step (v): Germanium layer 178 (1.5 µm thickness) was deposited over Cr/Au electrodes 176 using e-beam evaporation and patterned using lift-off technique to form sensing layer 180; SiO$_2$ (1.8 µm) deposited using PECVD over the sensing layer 180 and etched from the contact pads 182. The Cr/Au (0.02 µm/0.5 µm) film was deposited and patterned to form the contact pad 182 for the electrical connection to the tissue;

Step (vi): SU-8 pillars 154 (750-µm diameter and 100-µm height) wave patterned over the contact pad 182 and coated with a metal film 156 to make them electrically conductive.

The pillars 154 serve a dual purpose:

a) to act as the force transmitters to the biological tissue during tissue indentation; and b) to serve as electrically conductive electrodes (E2).

Front-to-back alignment was used to open the window 184 from the backside of the silicon wafer 132. The SiO$_2$ layer 170 was etched followed by silicon etching (350 µm) to form a 150 µm diaphragm. The fabricated biochip 22 was realized by subsequent dicing it from the silicon wafer 132 using a dicing saw.

Figure 8A:
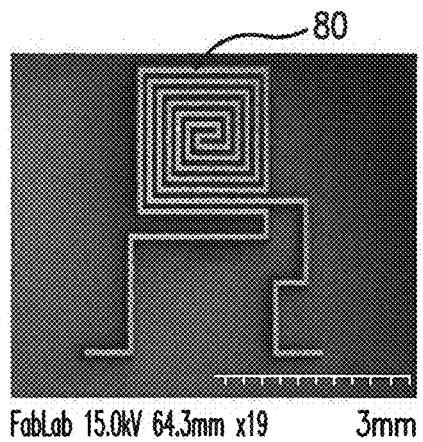
FIGS. 8A-8E are SEM images of the subject biochip manufactured with a micro-heater and electro-mechanical sensors, where
Figure 8B:
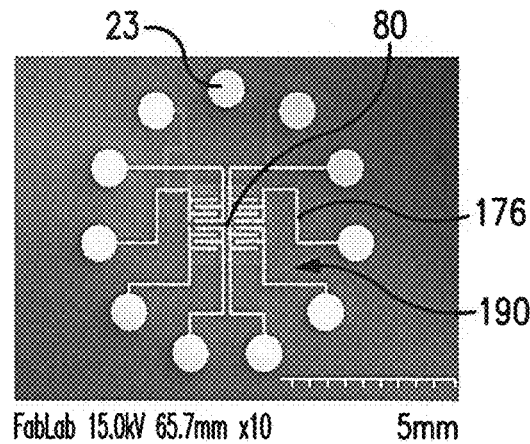
Figure 8C:
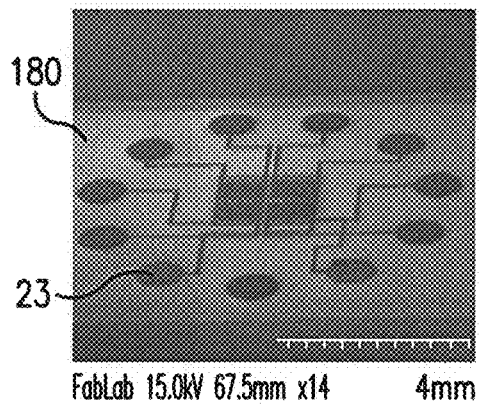
Figure 8D:
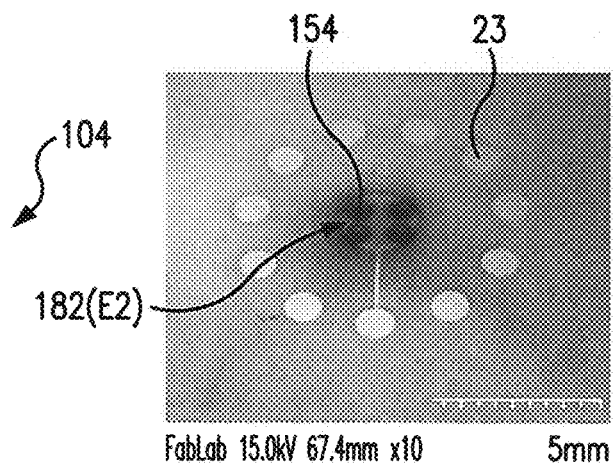
Figure 8E:
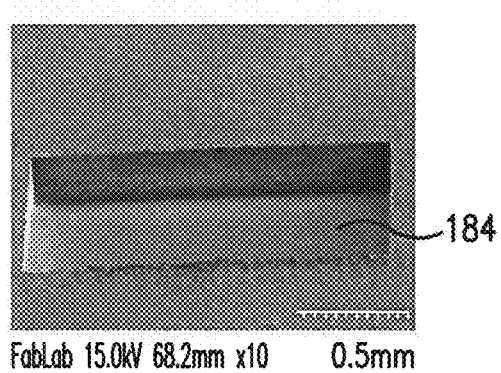
Figure 8F:
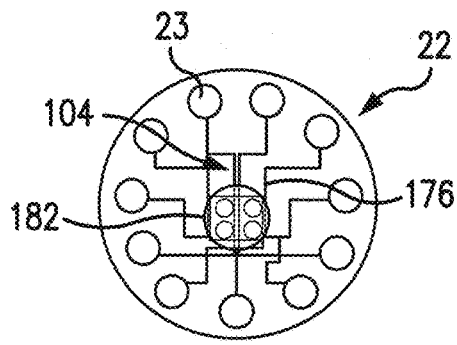
FIG. 8F is a schematic view of the subject biochip.
Figure 8G:
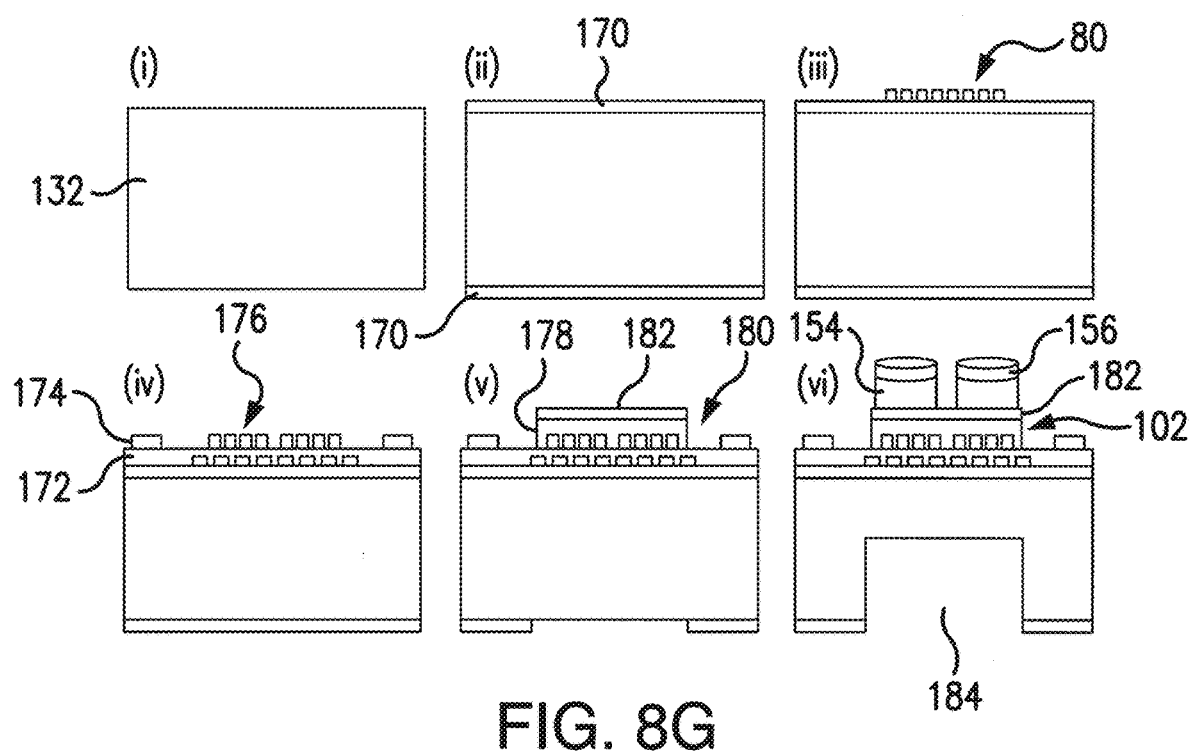
FIG. 8G is representative of the subject fabrication process flow for manufacturing the subject biochip with the micro-heater.
Figure 8H:
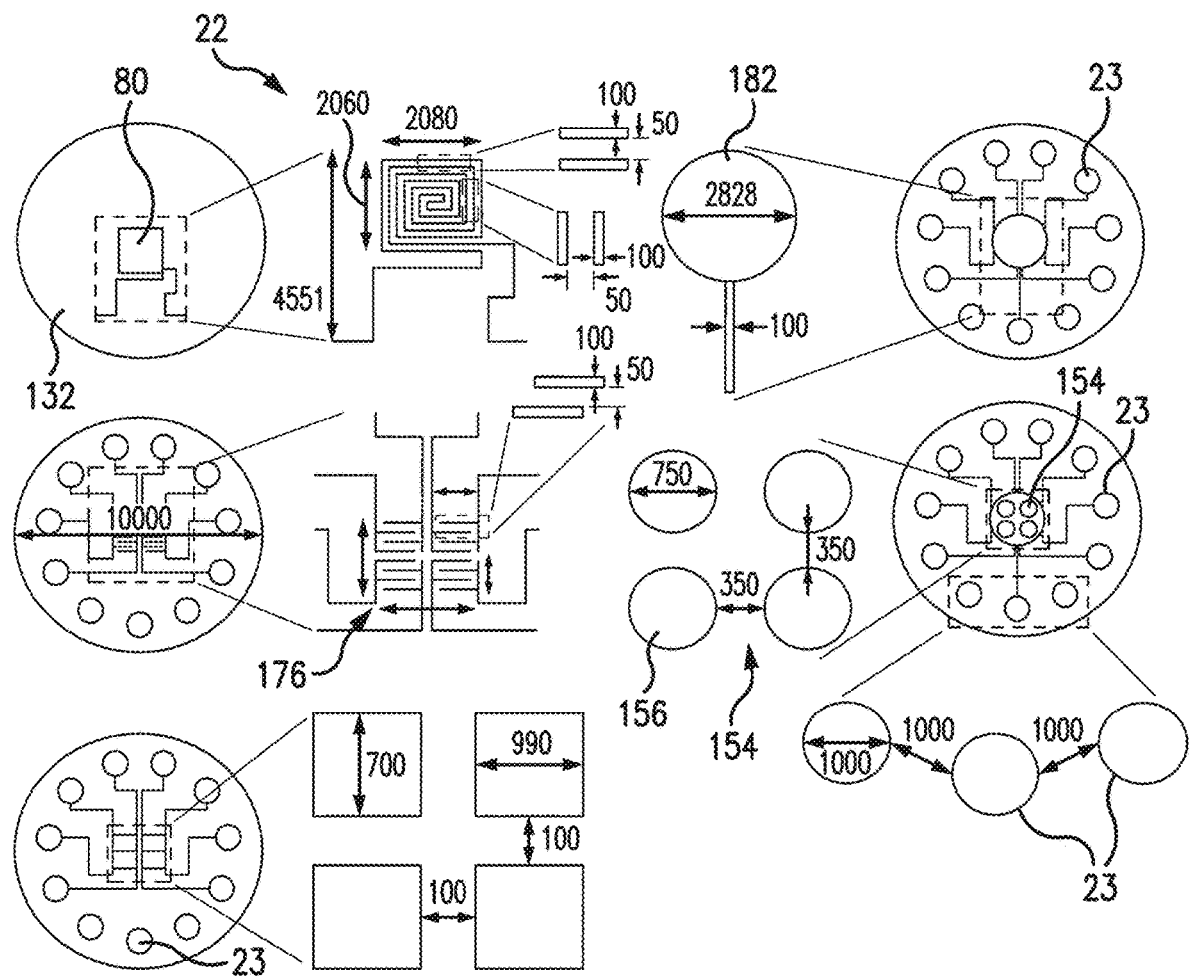
FIG. 8H is a schematic representation of the subject biochip showing dimensions of the biochip and sensor elements integrated therewith.

FIG. 8H shows the dimensions of the elements used in fabricating the biochip.

FIGS. 8A-8E are representative of the SEM images of the micro-heater 80 (FIG. 8A), interdigitated electrodes 176 (FIG. 8B), sensing layer 180 (FIG. 8C), gold electrode 182 for electrical contact, and SU-8 pillars 154 over the gold electrodes 182 (FIG. 8D), and the backside window 184 of the silicon diaphragm (FIG. 8E).

Experimental Setup

FIG. 3A-3B show the schematic diagram of the subject portable cancer diagnosis system 10. The system 10 was built with a MP-285 micromanipulator attached with an indenter 60 and a disposable biochip holder module 14 integrated with the biochip 22 for measuring properties of the biological tissue 76.

It is to be understood that the subject system is applicable to measurements of tissues of any part of a body and diagnosis of any type of cancer. However, as an example only, but not to limit the applicability of the subject system to this particular example, characterization and diagnosis of breast tissue samples is presented herein.

For the measurements, the tissue sample 76 was placed in the biochip holder module 14, which had the biochip 22 integrated therein. Connecting pins 94 were used on the PCB 92 for facilitating the incorporation of the biochip output to the data acquisition card 28 contained in the electronic box 26. The indenter 60 connected to the MP-285 micro-manipulator 62 was brought in contact with the tissue sample 76.

The micro-heater 80 was actuated to heat (in a controller manner) the tissue 76.

With the assumption that the sample tissues 76 are regarded as uniform structures, the measured temperature values were converted to thermal conductivity using $$q = \frac{kA\Delta T}{L_t} \tag{Eq. 1}$$

where q [W] is the rate of heat transfer through the tissue along the length of the tissue, k [W/mK] is the thermal conductivity of the tissue, A [m$^2$] is the cross-sectional area of the tissue, $\Delta T$ [K] is the temperature difference between bottom and top surface of the tissue, and L$_t$[m] is the thickness of the tissue.

In order to measure the electrical conductivity of the tissue, a constant voltage was applied between the top electrode (E1) and the bottom electrode (E2) on the biochip 22, as shown in FIG. 4C. The electrical path was complete when the top electrode (E1) touches the tissue sample and current passed through the top electrode E1 through the tissue to the bottom electrode E2 on the biochip 22. An output voltage (measured from a voltage divider) varies with respect to the resistivity of the tissue, which correspondingly depends on the type of the tissue [normal or cancerous (IDC)].

From an obtained SEM image of the tissue specimen, it was observed that the normal tissues show a smooth topography compared to cancerous tissues, which show ruptured structure. It is hypothesized that: 1) when the current passes through the tissue, the resistance fluctuates depending on the composition of the tissue; and 2) the cancerous tissues, being coarse in nature, provide a higher resistance path for current to flow compared to smooth structures of the normal tissues.

To measure the response of the micro-heater 80, a DC voltage from 0-1.8 V with increment of 0.2-V step was applied to the micro-heater, and the temperature of the tissue was measured by the temperature sensor 78. The steady-state values of the temperature at each voltage were measured and plotted. The best fit R$^2$-value obtained was 0.9966. It was observed that the difference between the surface temperature of the tissue and the measured temperature at the top of the tissue was very small.

The breast tissue was placed in contact with the biochip and heated from 25 to 50° C. with a 5° C. step increment using the integrated micro-heater. The thermal conductivity of the normal and IDC tissues was measured using heat conduction equation (using (Eq. 1). The thermal conductivity of normal and IDC breast tissues was plotted by measuring the temperature at the top end of the tissue sample using the thermistor placed on the indenter 60.

The two-sample t-test was conducted for the thermal conductivity data of normal and IDC groups of tissues to analyze data statistically. Apart from the first temperature range (20-25° C.), the rest of the data fell within p-value of 0.05. The p-value for the entire dataset was calculated as 0.000027, which shows statistically significant difference in thermal conductivity between normal and cancer tissue groups. This implies that the thermal conductivity of breast tissue can be used as a biomarker to differentiate normal tissue from cancerous breast tissue, once a sufficient number of measurement points are used.

In the case of a cancerous tissue specimen, the thermal conductivity of the tissue increased with increase in temperature, while in the normal tissues the change in the thermal conductivity did not show a particular trend. However, from the t-test, it was observed that the thermal conductivity values obtained were statistically different.

Figure 9A:
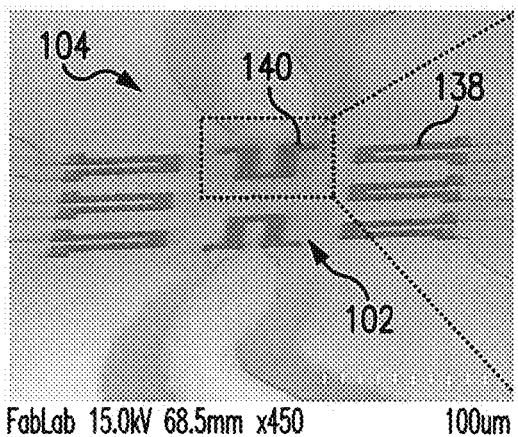
FIGS. 9A-9F are the SEM images corresponding to the biochip fabrication, with FIG. 9A showing the strain gauge array, FIG. 9B showing a single strain gauge, FIG. 9C showing the array of gold pads/$SiO_2$/strain gauges, FIG. 9D showing a magnified image of a single micro-sensor, FIG. 9E showing an array of gold coated SU-8 pillars/gold pads/$SiO_2$/strain gauges, and FIG. 9F depicting magnified images of the SU-8 pillars on the gold pads (with the inset showing gold-coated SU-8 gold pillars formed on the gold contact pads)
Figure 9B:
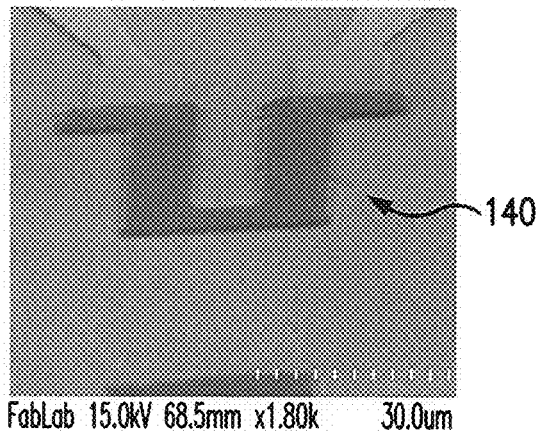

The scanning electron microscopy (SEM) images of the electro-mechanical sensor array 104 and a single strain gauge sensor 140 are shown in FIGS. 9A-9B, respectively. The strain gauge 140 is made from PEDOT:PSS polymer, which can withstand large strain due to its flexibility, while maintaining its conductivity. Each strain gauge 140 was 50 μm×70 μm in size.

Figure 9C:
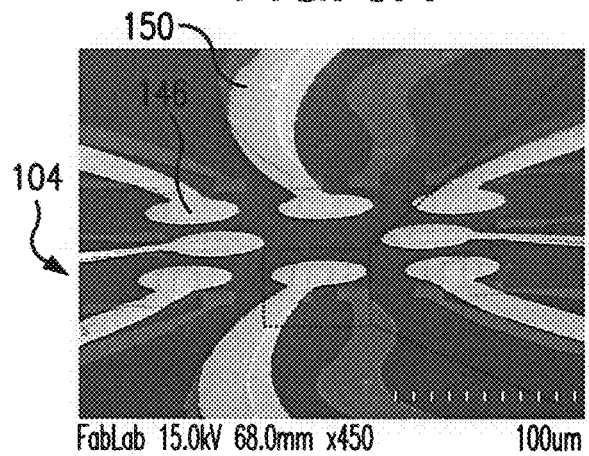
Figure 9D:
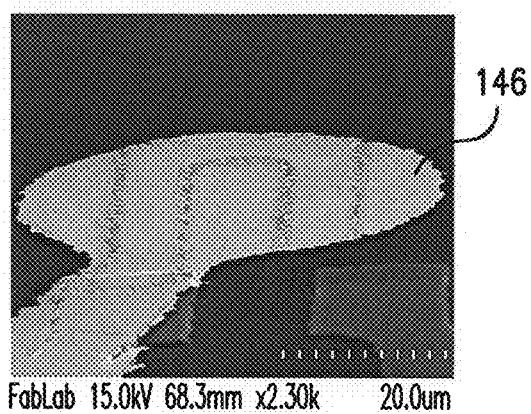
Figure 9E:
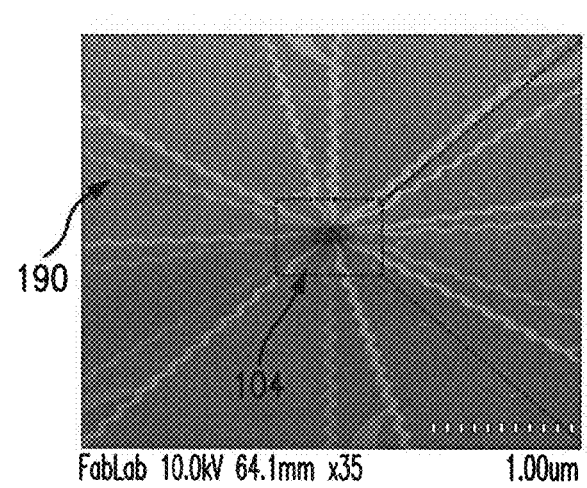
Figure 9F:
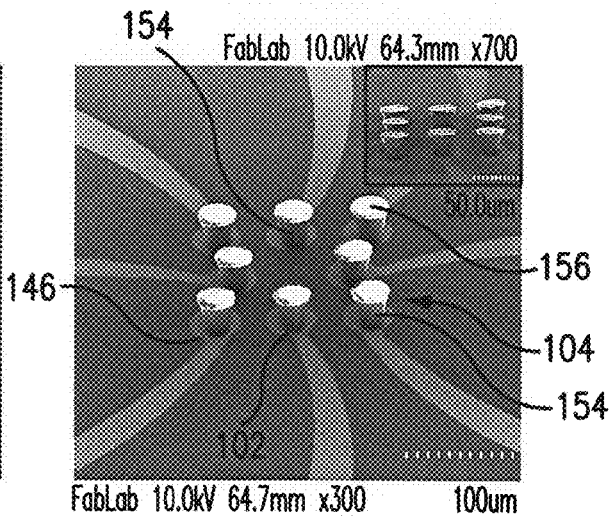

FIG. 9C shows an array 104 of Cr/Au electrodes/SiO$_2$/strain gauges. The circular Cr/Au pad (50 μm diameter) 146 was used as the base for electrical contact to the SU-8 pillar (FIG. 9D). FIG. 9E shows the array of conducting SU-8 pillars integrated on the gold pads, and FIG. 9F shows the magnified image of SU-8 pillars 154 on the gold pads 146 with the top surface shining due to metal coating 156. The coating 156 is provided only on the top and on one side of the SU-8 pillar 154 since it is necessary to obtain electrical contact from the tip of the SU-8 pillar to the base to enable the measurement of the electrical property of the tissue.

The pillars 154 serve a dual purpose in the biochip design, namely: (a) transferring the force to the strain gauge and (b) acting as the conductive probe for electrical characterization (Electrode E1).

The SU-8 pillar diameter was kept at 30 μm which has two advantages: (a) ease of alignment at the center of the gold pad 146, which was 50 μm in diameter, and (b) metal coating using lift-off technique is easy if the pillar size is smaller than the dimensions of the gold pad. The spacing between the pillars 154 was chosen to facilitate the metal coating 156 on SU-8 pillars.

Figure 10:
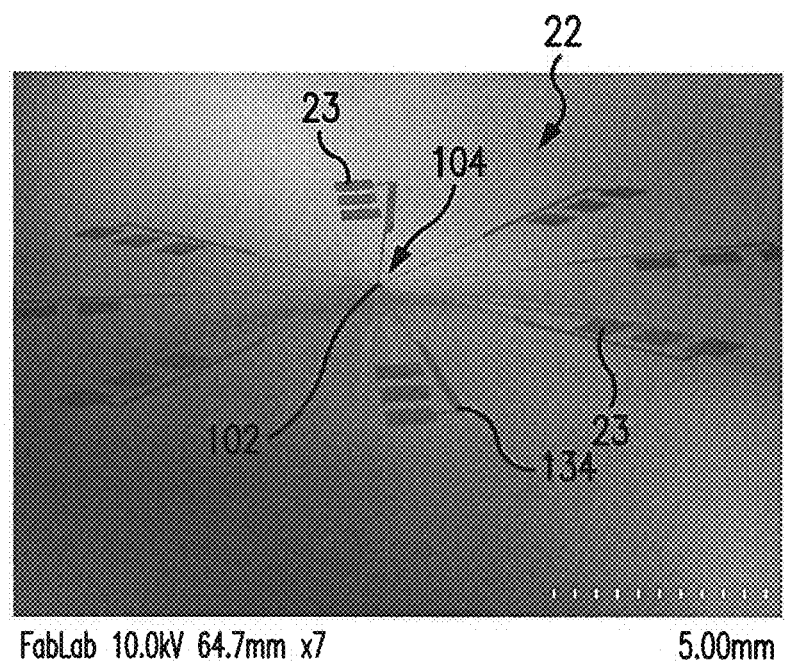
FIG. 10 depicts an SEM image of the subject biochip.
Figure 11:
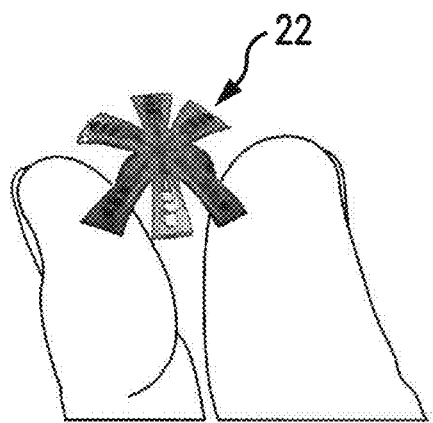
FIG. 11 shows the subject flexible MEMS-based device (biochip)

The SEM image of realized biochip is shown in FIG. 10, while FIG. 11 shows the flexible electro-mechanical biochip 22.

Figure 5A:
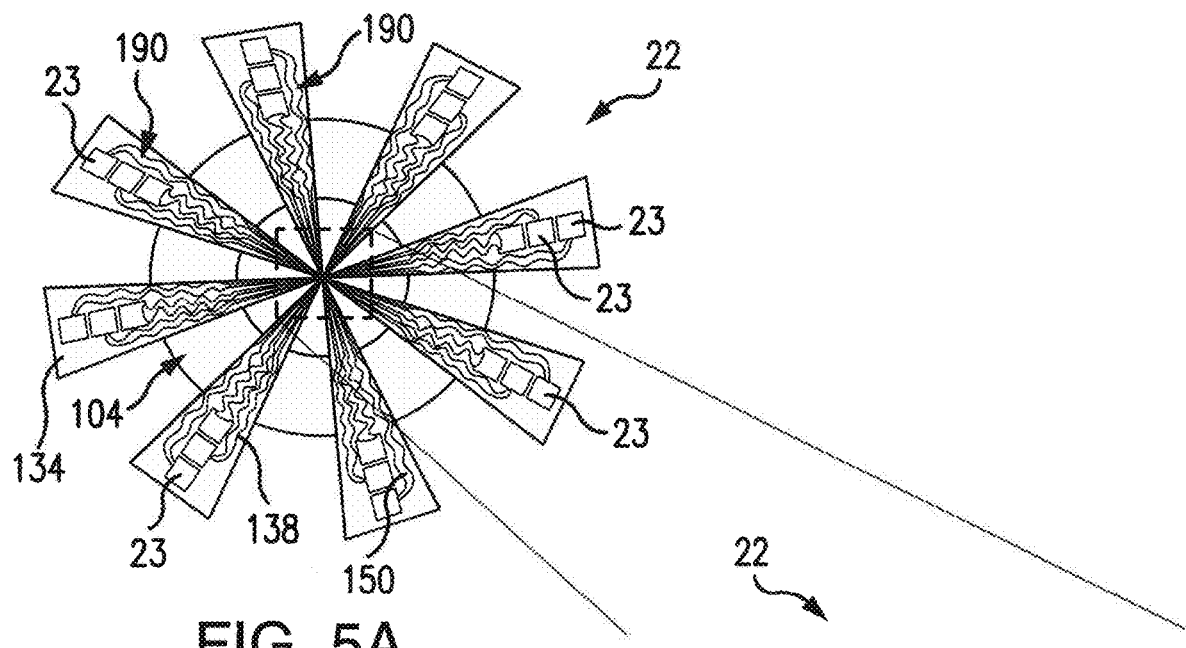
FIG. 5A is a schematic diagram of the flexible MEMS device (biochip) showing contact pads for the micro-sensor array.
Figure 5B:
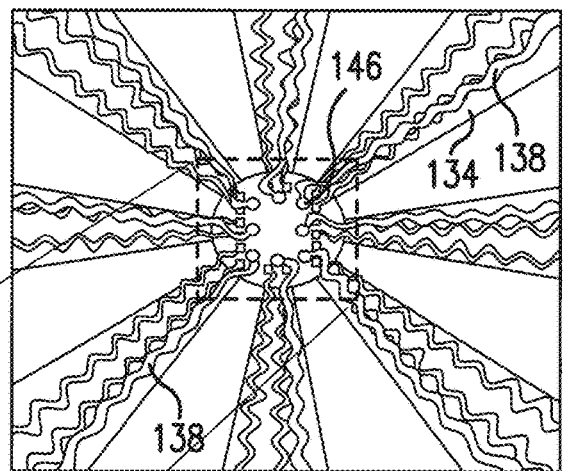
FIG. 5B is a magnified schematic top view of the subject biochip.
Figure 5C:
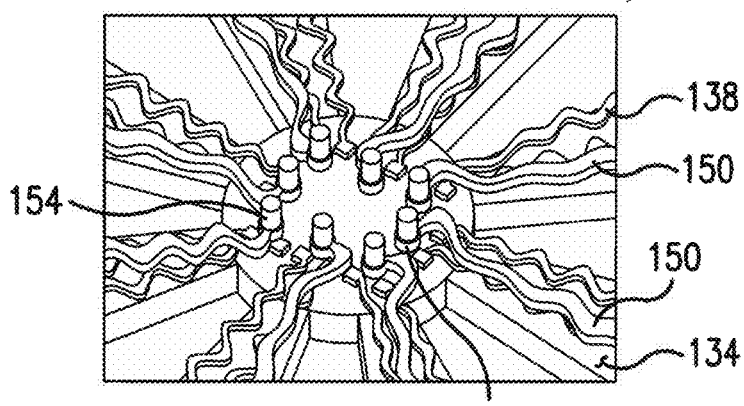
FIG. 5C is a magnified angled view of the subject biochip.
Figure 6A:
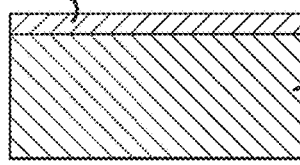
FIGS. 6A-6M are representative of the subject manufacturing process flow for fabrication of the subject flexible biochip with the electro-mechanical sensor array.
Figure 6F:
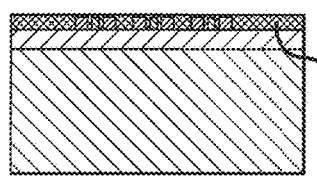
Figure 6J:
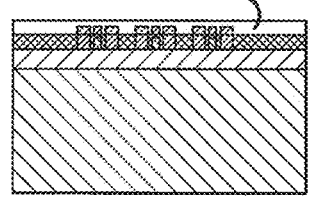
Figure 6B:
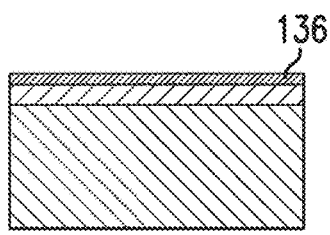
Figure 6G:
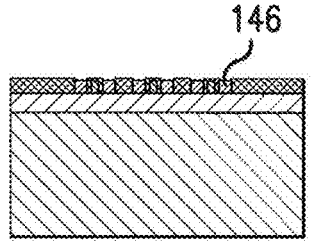
Figure 6K:
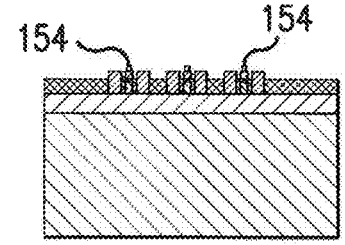
Figure 6C:
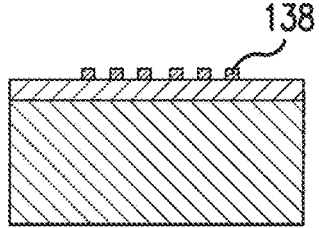
Figure 6H:
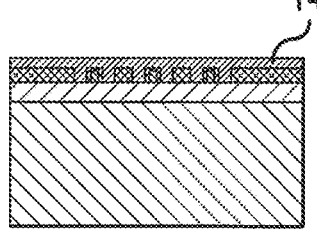
Figure 6L:
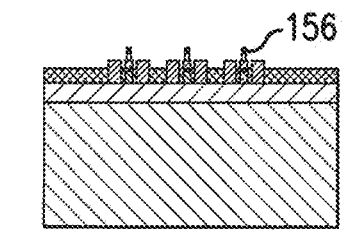
Figure 6D:
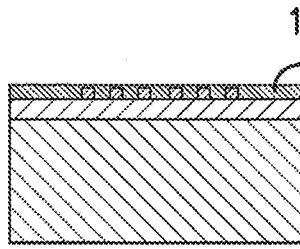
Figure 6I:
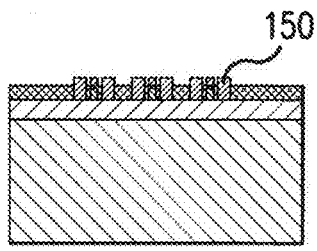
Figure 6M:
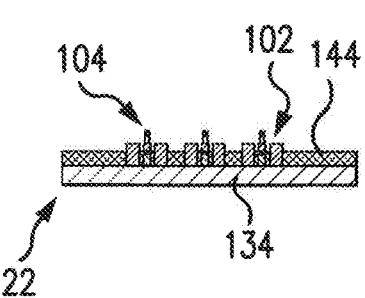
Figure 6E:
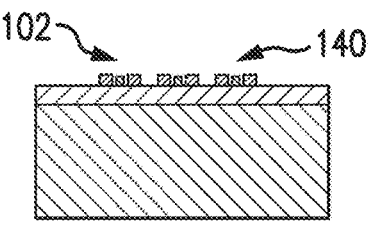

As shown in FIGS. 5A-5C, the connection from the electro-mechanical sensor array 104 to the contact pads 23 (1 mm×1 mm) is through the Gold serpentine geometry 190 to enable a compact footprint for routing the measured signal to the external electrical circuit 24.

Figure 12B:
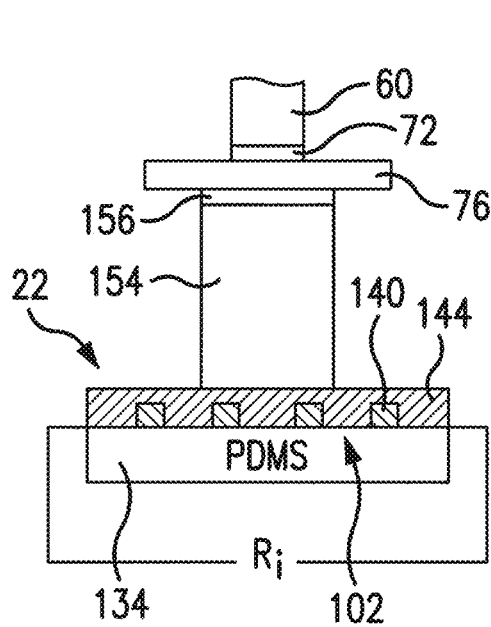
FIGS. 12B-12C show a schematic representation of the strain sensing mechanism for the subject PEDOT:PSS based sensor (biochip) under zero applied force (FIG. 12B) and with a force applied to the SU-8 pillar during measurements (FIG. 12C)
Figure 12C:
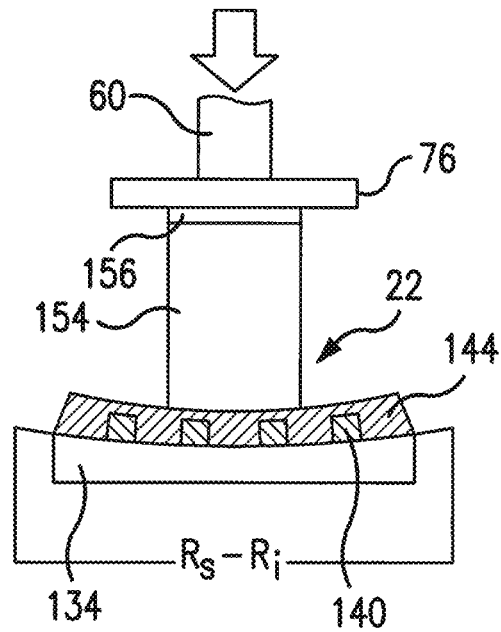

Referring to FIGS. 12A-12C, the pillars 154, during measurements, are brought in contiguous contact with the tissue sample core 76. For the measurement routine, the biochip 22 and the tissue 76 are brought in alignment, and the indenter 60 is subsequently lowered (in a controlled manner) for achieving contact between the pillars top 156 and the tissue sample. Due to the piezoresistive effect, the electrical resistance of the film is proportional to the strain of the film. The schematic diagram of strain sensing mechanism is shown in FIGS. 12B-12C.

The known force value using the AFM cantilever was applied on the SU-8 pillar 154 resulting in bending of the strain sensor 140, and the corresponding change in resistance was measured.

The gauge factor G is given by the following relationship:

$$G\varepsilon = \frac{\Delta R}{R_i} = \frac{R_s - R_i}{R_i} \quad \text{(Eq. 2)}$$

where ε, $R_i$ and $R_s$ are the strain, initial resistance of the sensor, and sensor resistance on a curved surface, respectively.

The gauge factor calculation determines the strain from the change in resistance. When the strain gauge integrated on the flexible substrate was deformed to form the curved surface, it resulted in surface strain ε given by:

$$\varepsilon = \frac{t}{2r} \quad \text{(Eq. 3)}$$

where r is the radius of curvature and t is the substrate thickness.

Figure 13A:
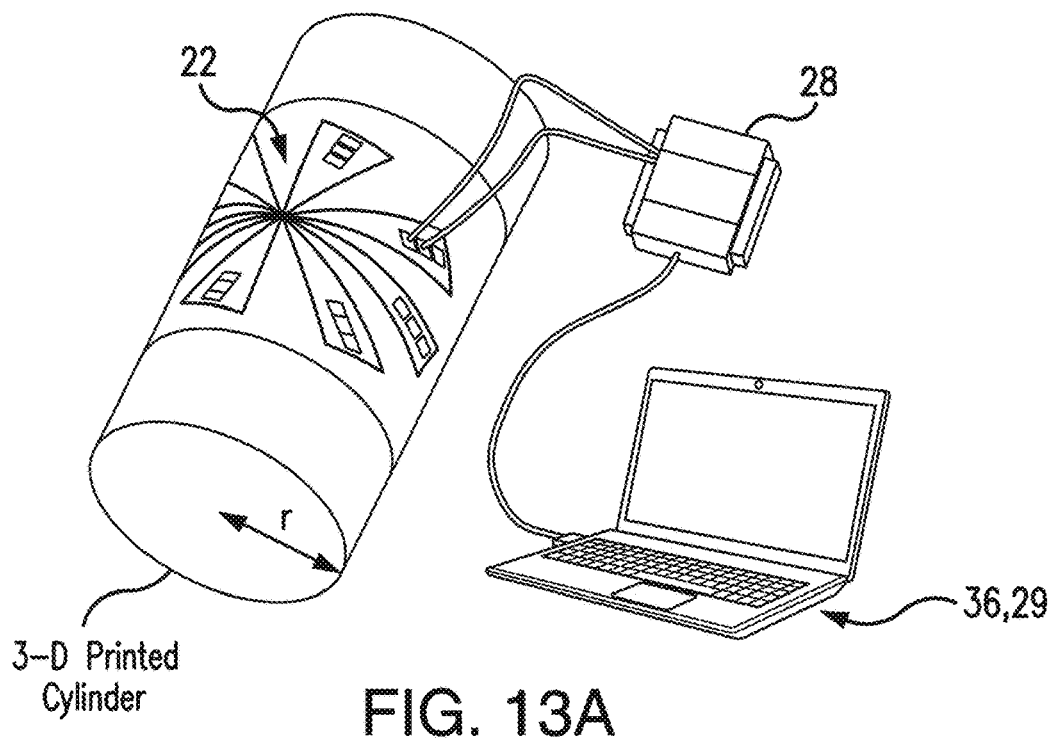
FIG. 13A is a schematic representation of a measuring routine for calibrating an electrical output from the subject single strain sensor on a 3-D printed cylinder.
Figure 13B:
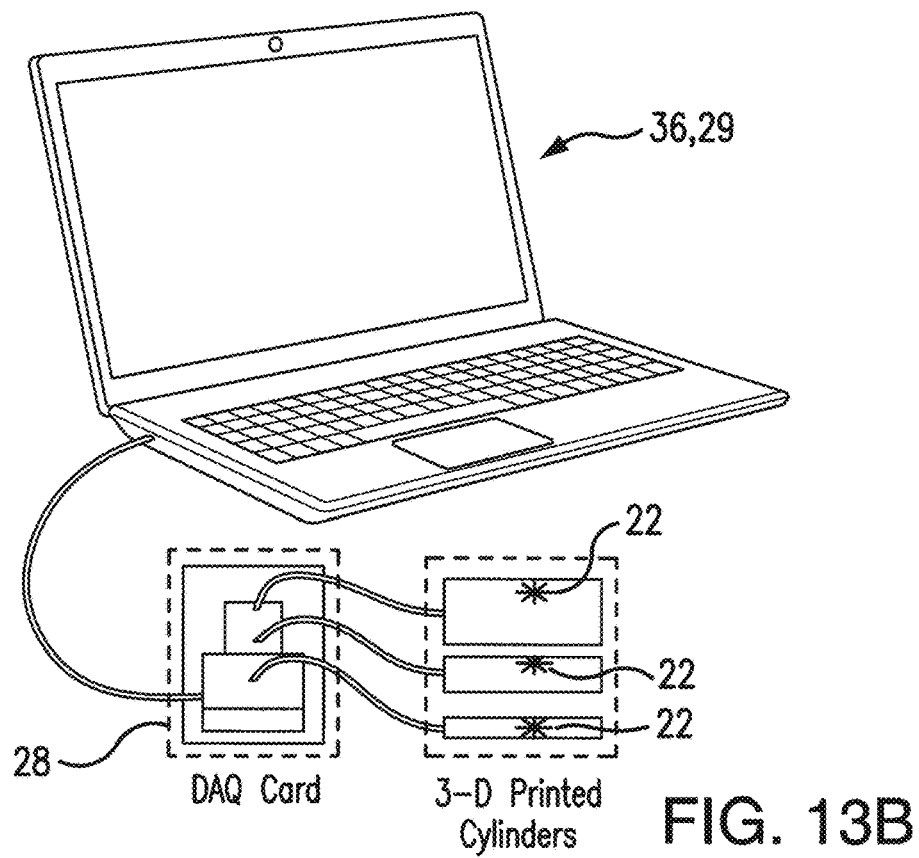
FIG. 13B illustrates the experimental set-up for the electrical measurements.

The substrate (PDMS) thickness was 140 μm in the experiment. To measure the gauge factor of the strain gauges, the flexible biochip 22 was placed on the curved surface of cylinders with different radii. The schematic representation and photo of the actual measurement setup for measuring the gauge factor is shown in FIGS. 13A-13B.

The change in resistance ΔR, strain ε and gauge factor G were subsequently calculated. The resistance of the strain gauges was measured to be 1.2±0.1 kΩ in its non-deformed configuration. The induced strains in the sensor were found to be 1.4, 0.7 and 0.35, respectively, when placed on the cylinder with radii of 5 mm, 10 mm and 20 mm, respectively. Using Eq. (2), the measured gauge factor of the sensor was determined to be 4.0±0.1.

Linear Regression Model

For accurate estimation of material properties of the tissue, researchers have studied contact models that describe tissue behaviors and algorithms finding contact point between a sensor and tissue. Since most of the tissue contact models are based on force-indentation relationship, piezoresistive type sensors that have resistance as an output may be calibrated in terms of force to be applied to conventional contact models.

For a number n of data sets in calibration, the output resistance $R_s$ and contact F have a linear relationship to the sensor deformation $\delta_s$ when contact occurs at the $k^{th}$ index. Thus:

$$(R_s)_i = \begin{cases} \alpha_{11} + \alpha_{12}(\delta_s)_i + \varepsilon_1 & \text{if } i \leq k \\ \alpha_{21} + \alpha_{22}(\delta_s)_i + \varepsilon_2 & \text{if } k+1 \leq i \leq n \end{cases} \quad \text{(Eq. 4)}$$

$$F_i = k_s \delta_s = \begin{cases} k_s \left[\frac{(R_s)_i - \alpha_{11} + \varepsilon_1}{\alpha_{12}}\right] & \text{if } i \leq k \\ k_s \left[\frac{(R_s)_i - \alpha_{21} + \varepsilon_2}{\alpha_{22}}\right] & \text{if } k+1 \leq i \leq n \end{cases} \quad \text{(Eq. 5)}$$

where the values $\alpha_j = [\alpha_{j1} (\Omega) \; \alpha_{j2} (\Omega/\mu m)]$ (j=1, 2) are linearly regressed parameters in the non-contact and contact regime, respectively; $k_s$ is the calibrated spring constant of the sensor, and $\varepsilon_j$ (j=1, 2) are the errors that typically have different distribution depending on the material interaction with the sensor.

In this model, $\varepsilon_1$ is caused by the viscous interaction between the biochip and the phosphate-buffered saline (PBS) solution covering the tissue, while $\varepsilon_2$ are primarily results from sensor-tissue friction. Material properties in conventional contact models vary with the determination of contact point within the same data set.

The contact point can be determined by a variety of methods such as estimating the location of a threshold slope, curve fitting, and statistical modeling. One of the advantages of the developed sensor is that it allows current flow on contact and hence it acts as a switch to detect when the contact has occurred.

In AFM studies for tissue indentation, the deformation depth of tissue $\hat{\delta}_t$ can be calculated in the contact region (k+1≤i≤n) as the difference of sensor deflection with respect to sensor position in the Z direction as shown in (Eq. 6). Thus:

$$(\hat{\delta}_t)_i = \Delta Z_s - \delta_s = (Z_s)_i - (Z_s)_k - \frac{(R_s)_i - \alpha_{21} + \varepsilon_2}{\alpha_{22}} \quad \text{(Eq. 6)}$$

By using the tissue deformation and force data, the elastic modulus of tissue can be estimated by Zhang's contact model of a cylindrical tip that requires geometric information (of the tissue and the indenter), reaction force, and tissue deformation depth.

Spring Constant Measurement

Figure 14A:
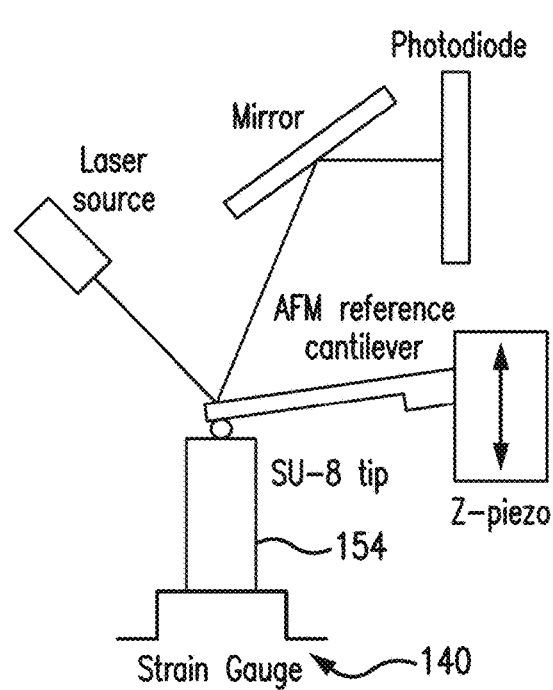
FIGS. 14A-14C are schematic diagrams of the AFM configuration used for spring constant measurement of PEDOT:PSS strain gauge using reference cantilever method, with FIG. 14A being a 2-D representation of the AFM cantilever in contact with (but not pressed against) the SU-8 pillar/strain gauge, FIG. 14B showing the AFM cantilever pressed against the SU-8 pillar/strain gauge to a preset force value, and FIG. 14C being a 3-D representation of the methodology for the spring constant measurements in the subject system.
Figure 14B:
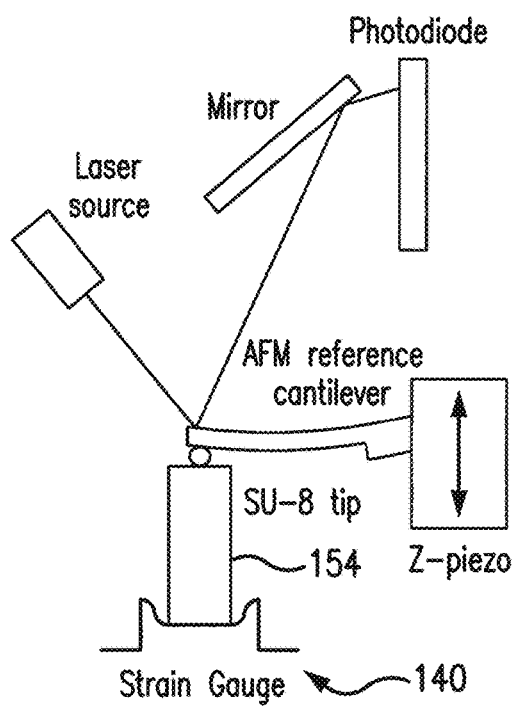
Figure 14C:
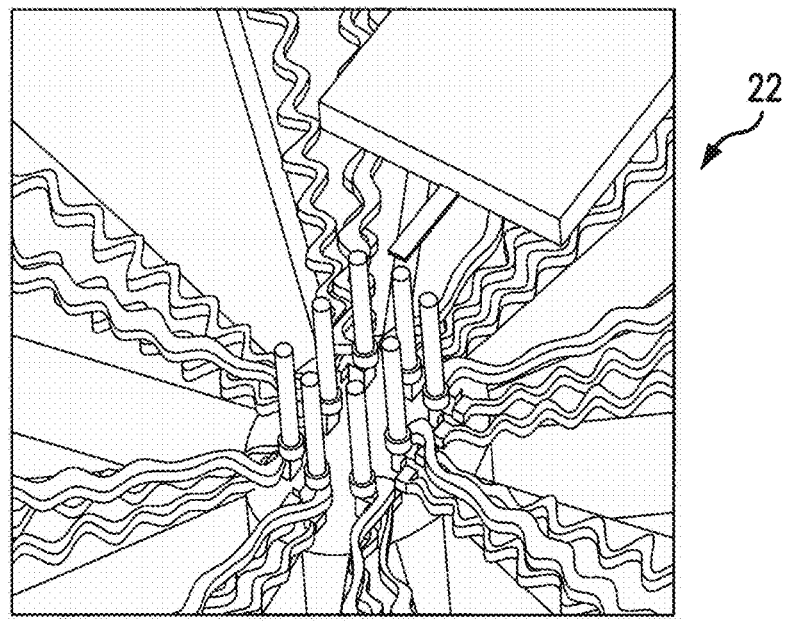
Figure 15:
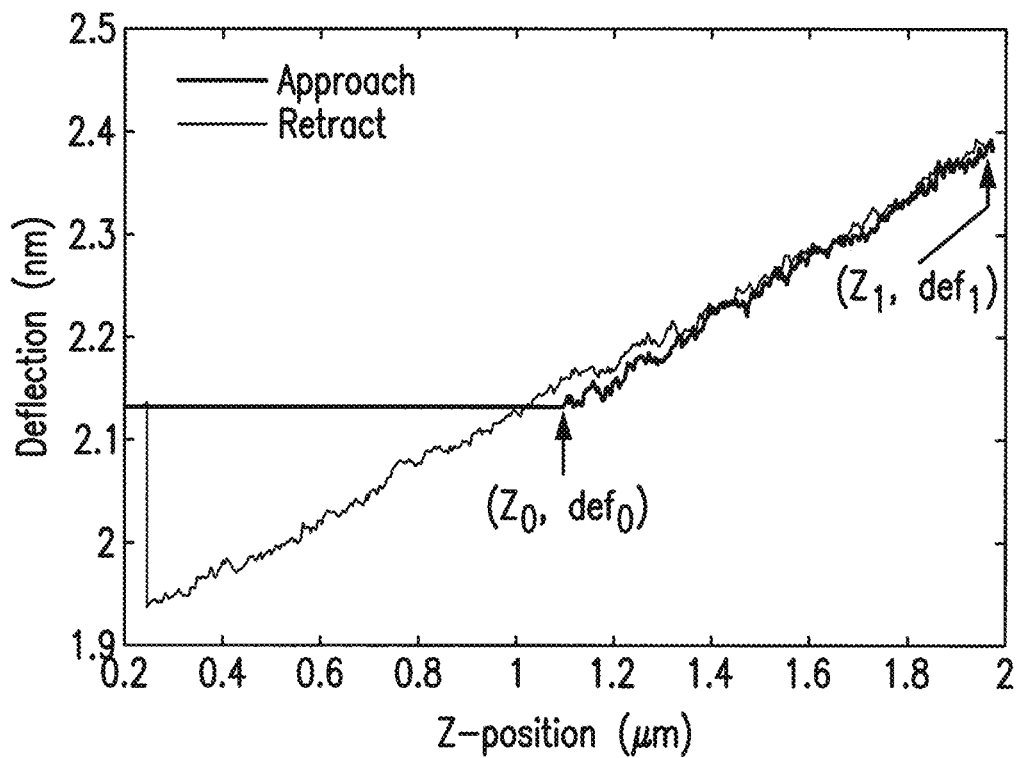
FIG. 15 is a diagram representative of the AFM force curve on the biochip (specifically, the SU-8 pillar/strain gauge/PDMS substrate showing deflection vs. Z-position)

To measure the spring constant of the strain gauge sensor, an AFM probe (pre-calibrated) was used as a reference cantilever and pressed on the SU-8 pillar with a known force (as shown in FIGS. 14A-14C).

The spring constant $k_{ref}$ of the AFM probe was calibrated using the thermal method. The AFM force curve was obtained from the end of test cantilever upon pressing the SU-8 pillar. The measured transmitted force is given by:

$$F_{AFM} = k_{ref}(\text{def}_1 - \text{def}_0) \quad \text{(Eq. 7)}$$

where, $\text{def}_0$ and $\text{def}_1$ are the initial and final deflection of the AFM cantilever which is sensed by the photodiode (as presented in FIGS. 14A-14C and 15). The deflection in the sensor, $\delta_s$, is given by the difference in the net deflection of the test cantilever and Z-travel.

Figure 16:
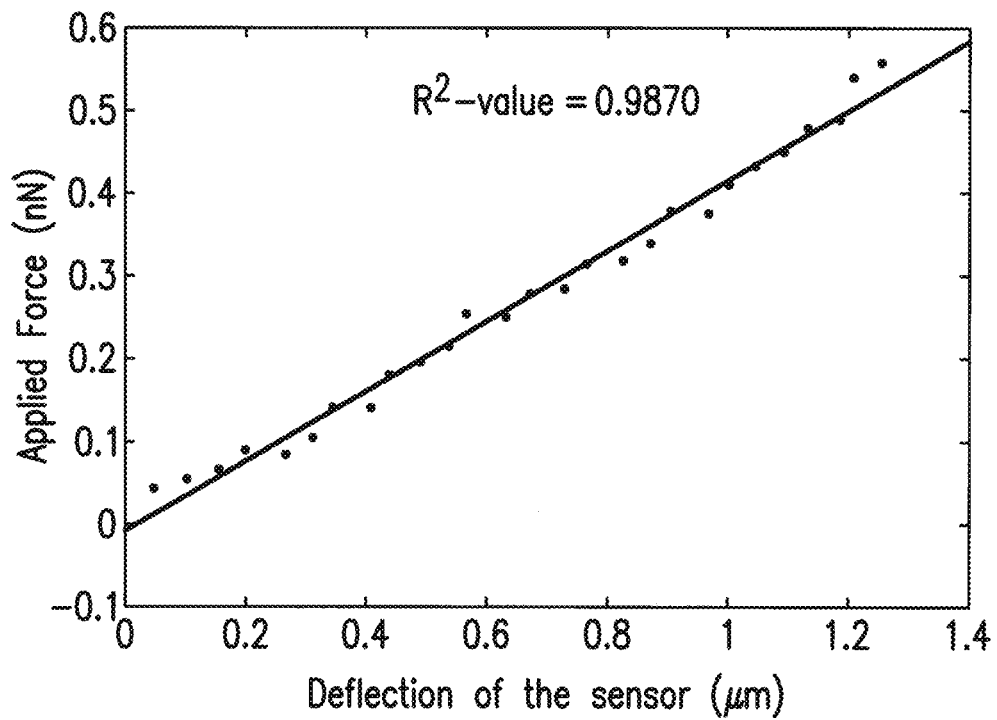
FIG. 16 is a diagram representative of the spring constant measurement of the subject biochip sensor showing applied force vs. deflection of the biochip sensor.

FIG. 16 shows the deflection of the sensor $\delta_s$ for increasing force values. The spring constant of the fabricated sensor was 0.42 nN/μm. The goodness of fit ($R^2$-value) was found to be 0.9870, which shows that the biochip has a linear response.

Tissue Preparation and Annotation

Figure 17A:
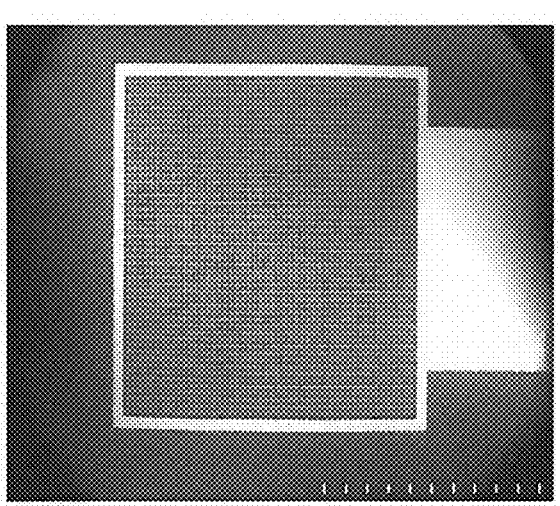
FIGS. 17A-17C are SEM images of the micro-grid (FIG. 17A), crumpled micro-grid (FIG. 17B), and breast tissue core placed on the micro-grid (FIG. 17C)
Figure 17B:
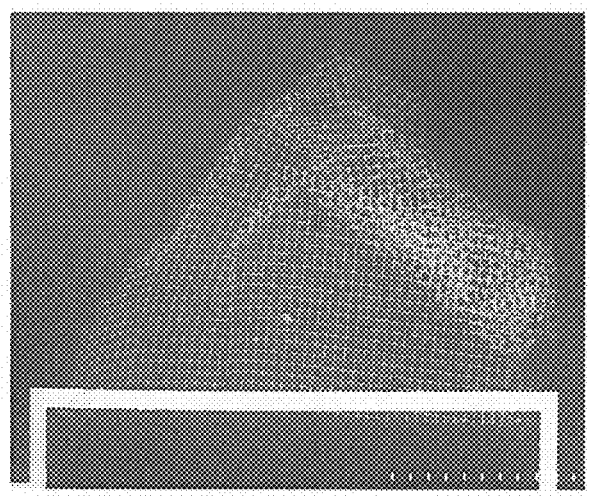
Figure 17C:
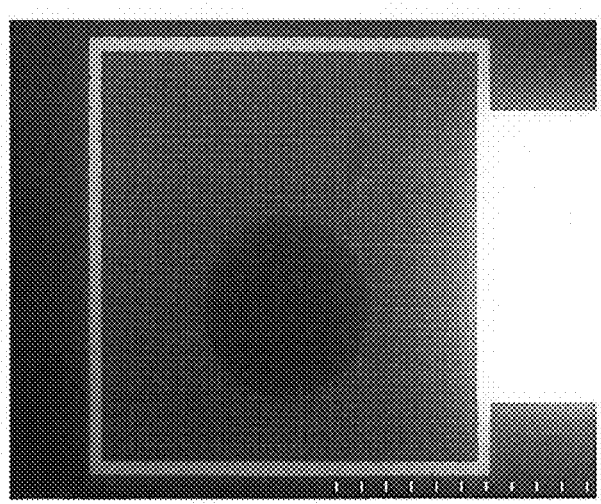
Figure 18A:
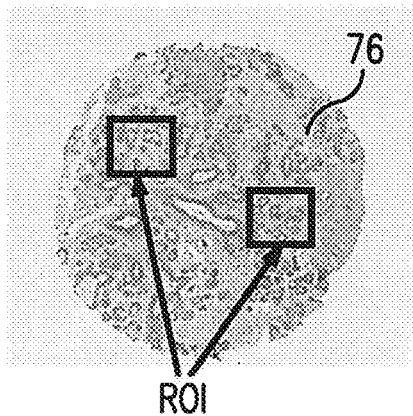
FIGS. 18A-18B show an H&E image (FIG. 18A) and an optical image (FIG. 18B), respectively, of a benign breast tissue sample.
Figure 18B:
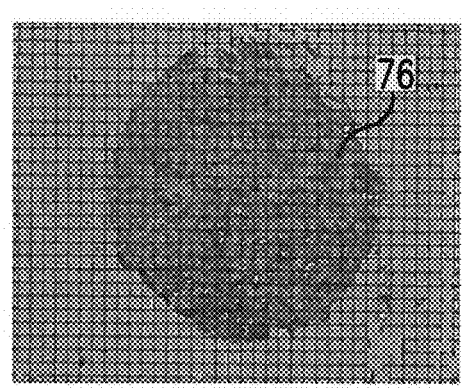
Figure 18C:
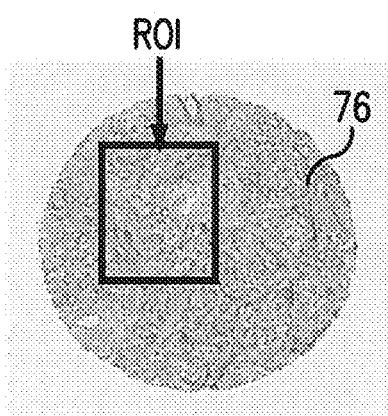
FIGS. 18C-18D show an H&E image (FIG. 18C) and an optical image (FIG. 18D), respectively, of a cancerous tissue sample.
Figure 18D:
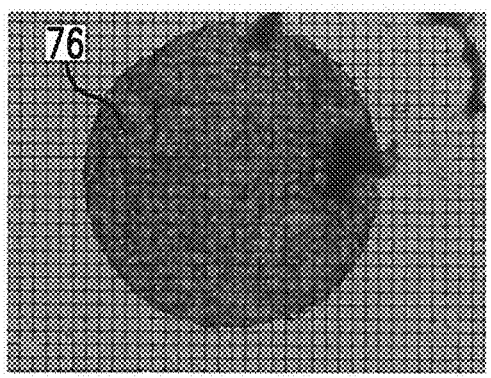

To facilitate the electro-mechanical characterization of the tissue, a gold pad having micro-grids (Electrode E2) was fabricated on a glass wafer to hold the tissue 76. Cr/Au (20 nm/800 nm) was deposited using e-beam evaporation and patterned to form micro-grids. FIGS. 17A and 17C show the SEM images of the gold pad having micro-grid and tissue placed on micro-grid, respectively.

The glass wafer needs to be moisture free to enhance the adhesion of Cr/Au. Failure to which resulted in the crumpled micro-grid as shown in FIG. 17B.

The inverted microscope was used for observing the tissue samples, and thus a grid was used instead of using a thick pad. The tissue was placed on the conducting micro-grid. Formalin-fixed paraffin-embedded (FFPE) tumor and normal breast tissue blocks were carefully identified from Biospecimen Repository at Rutgers Cancer Institute of New Jersey.

With the guidance of an annotated adjacent hematoxylin and eosin (H&E) slice, one sample of tissue core (1 mm diameter) was extracted from each tissue block and inserted into an individual pre-punctured paraffin block to make a mini-tissue microarray (TMA) using tissue microarrayer Breecher ATA-27. The mini-TMAs were sectioned at 8 μm thickness and placed at the center of the gold pad containing micro-grids in 42-44° C. water bath. The TMAs placed on the grids were de-paraffinized and stored in PBS solution until the experiment. An adjacent 5 mm section of each mini-TMA was stained, digitized into whole slide image, as well as quality controlled and annotated by a certified pathologist.

The whole slide images, with designated tissue regions highlighted as tissue annotation were stored at the Rutgers Cancer Institute of New Jersey whole slide image web service. FIGS. 18A-18D show the (H&E) and optical image of benign and cancerous breast tissue used in the experiments, respectively.

Sensitivity Measurement and Sensor Performance of the Tissue Sample

Figure 19:
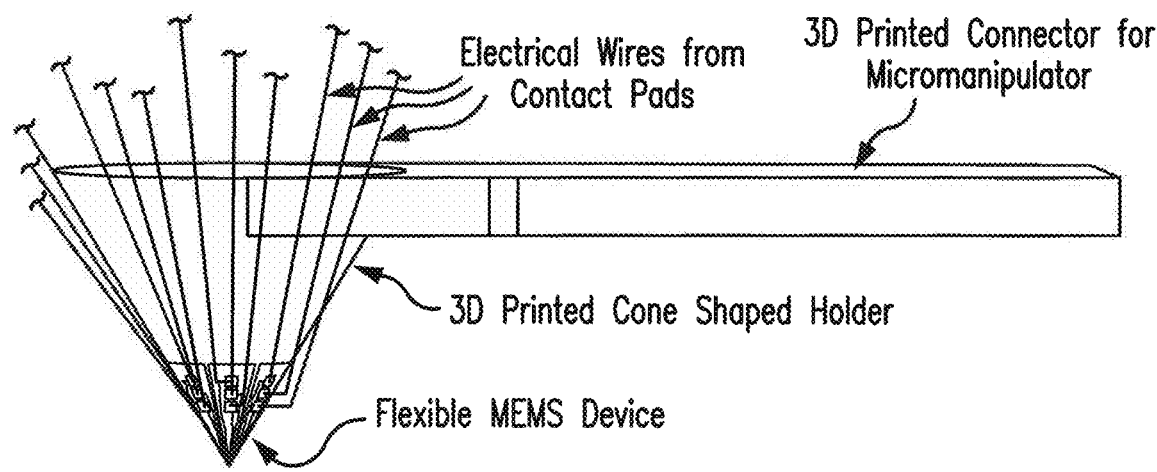
FIG. 19 is a schematic representation of the subject biochip mounted on a cone shaped holder for mechanical and electrical characterization of a tissue under study.

The strain gauges used for mechanical characterization change their resistance on applying strain and these strain values were measured to voltage by an electronic module including a multiplexer and data acquisition card. To measure the sensitivity of the sensor array, the biochip was mounted on a 3D printed cone shaped holder (FIG. 19) which was attached to the micro-manipulator MP-285. Using MP-285, the biochip was pressed down on a glass substrate to measure its sensitivity.

The right angle contact during the measurement was assumed. Since the biochip output caused by bending of the pillar from inclined indentation are not distinguished from the output of z-direction compression of the pillar that it was intended, it was assumed that the pillar contacts the tissue at the right angle (90 degree).

To avoid an inclined contact, the area of the biochip where the pillars are located was mounted on the flat tip of the cone shape holder and maximum height of the profile (i.e. difference between maximum peak height and maximum valley depth) of the tissue was under 0.5 μm, which was much smaller compared to the dimension of the pillars.

Figure 20:
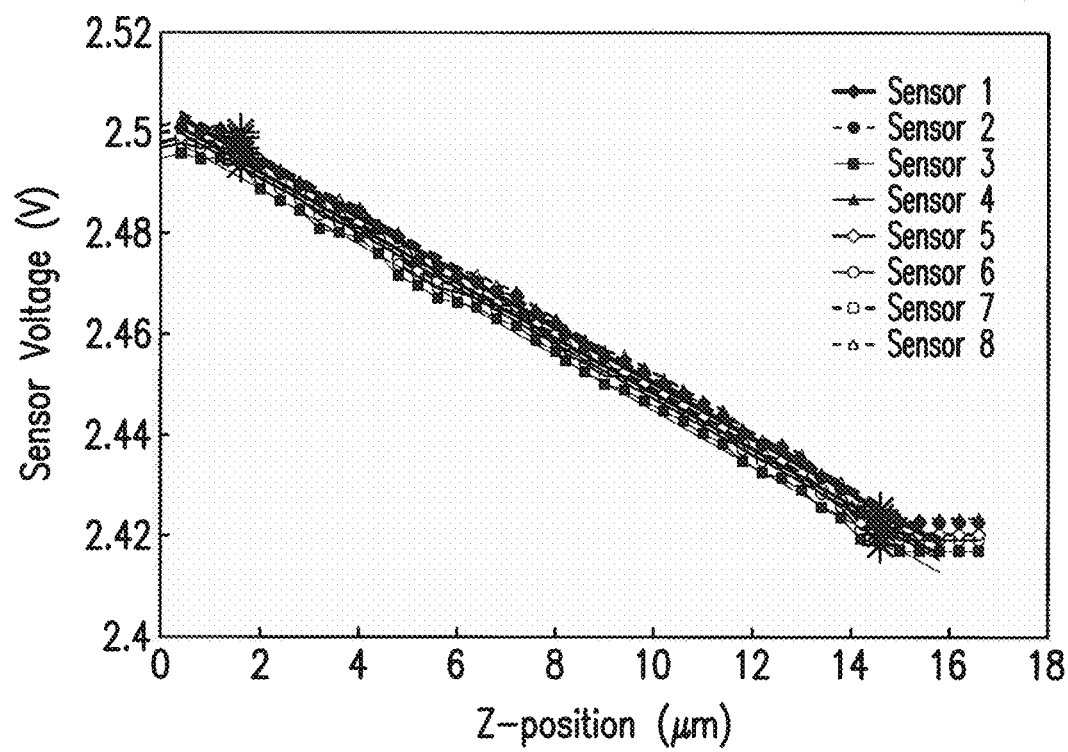
FIG. 20 is a diagram representative of the sensitivity measurement of the fabricated sensor array.

A linear regression model was used to find the correlation between the changes in the sensor reading to the sensor displacement (as shown in FIG. 20), which is the output voltage obtained from the sensor array and is a linear fit when pressed on the glass substrate.

The data obtained was used to calculate the force from each sensor using a linear regression model. The average goodness of fit ($R^2$-value) was found to be 0.9966, which shows that the sensor has a linear response. The average sensitivity of the eight sensors was found to be $4.2308 \times 10^{-4}$ V/μm.

Figure 21A:
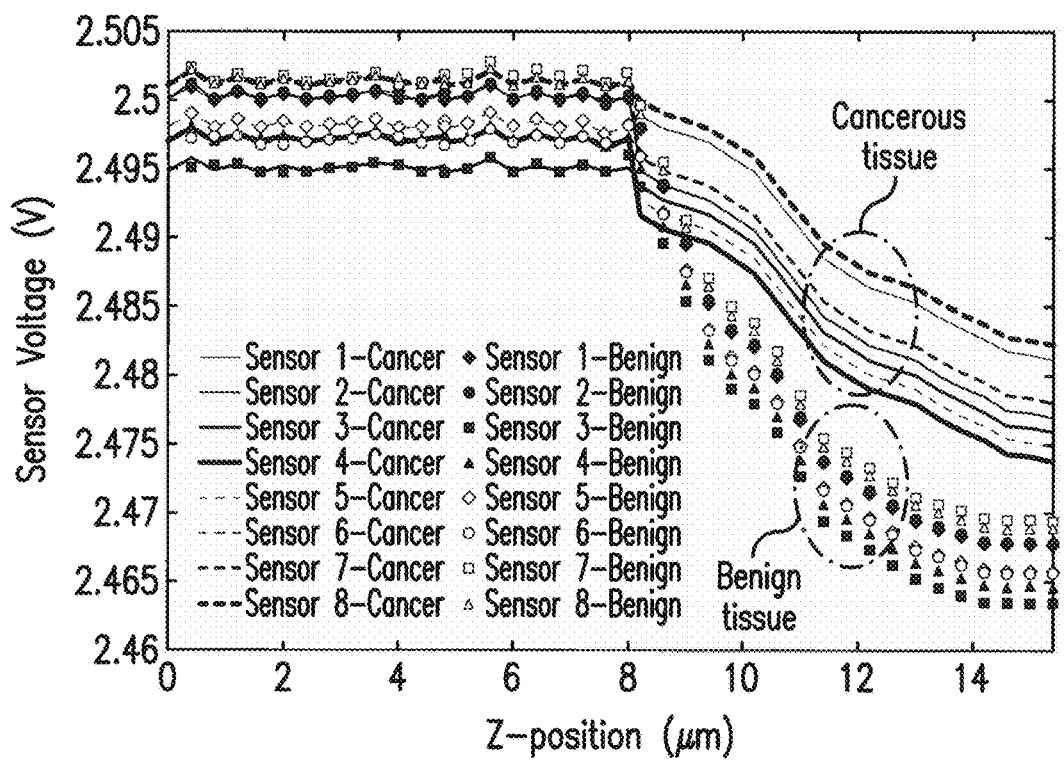
FIG. 21A is a diagram representative of the mechanical characterization of a tissue sample comparing response (sensor voltage) of the subject device for benign and cancerous tissue samples.

The sensor was pressed on benign and cancerous tissue for 7 μm. A clear demarcation between benign and cancerous breast tissue cores was obtained. It was further observed that, for the same z-displacement, the change in voltage for a benign core was higher than that for the cancerous breast tissue core (as shown in FIG. 21A).

Figure 21B:
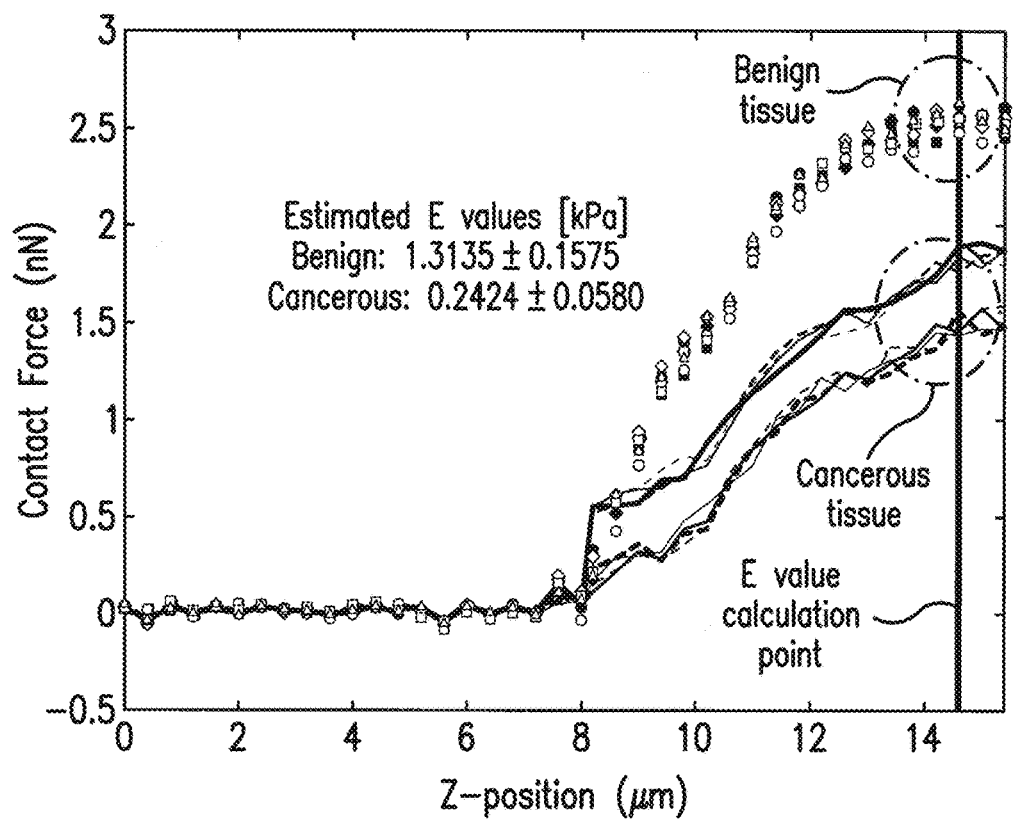
FIG. 21B is a diagram representative of the force curves obtained from normal and cancerous tissues.

The force has been plotted vs. Z-position obtained from the benign and cancerous breast tissue by pressing the sensor array on the tissue for 7 μm depth (as presented in FIG. 21B).

The tissue elasticity was estimated by using Zhang's contact model with a cylindrical tip and was given by:

$$E = \frac{F(1-v^2)}{2r\kappa\delta_t} = \frac{k_s\delta_s(1-v^2)}{2r\kappa(\Delta Z - \delta_s)} \quad \text{(Eq. 8)}$$

where F is contact force, v is Poisson's ratio, r is the radius of indenter, $\delta_t$ is the tissue deformation, and κ value is a unitless coefficient determined by the geometry of the indenter.

The spring constant of the sensor and the sensor deflection were obtained from the measured spring constant and linear regression model, respectively. Multiplication of these two values yields contact force and $\delta_t$ was determined by the difference between Z-position of the manipulator and sensor deflection. By using the table of κ-values, assuming that the tissue is incompressible, the elasticity of the tissue can be determined.

The values of tissue elasticity estimated from the observed reaction force when the sensor was pressed down to 7 μm on benign and cancerous tissues were 1.3135±0.1575 [kPa] and 0.2424±0.0580 [kPa], respectively. It is important to note that since the sensor is also inherently flexible, not all of the 7 μm motion of the tissue after contact with the tissue has been established were translated to the deformation of the tissue. The sensor motion remained at 7 μm constant in all trials for consistency.

The results of the experiments indicated that for the micron size breast tissue, the stiffness of normal tissues is higher than cancerous tissue cores. For the micron size breast tissue core (8 μm thick in the present case), the electrically conductive SU-8 pillars (E1) provides a simple way to complete the electrically conducting path. The height of the SU-8 pillars was kept at 50 μm as it facilitated in electrical measurements without breaking. Increasing the height of pillars to 100 μm could cause breakage of pillars while decreasing the size to 20-30 μm could make electrical measurements difficult. To measure the electrical resistance of the breast tissue, a constant voltage was applied between electrode E1 and electrode E2.

Figure 22:
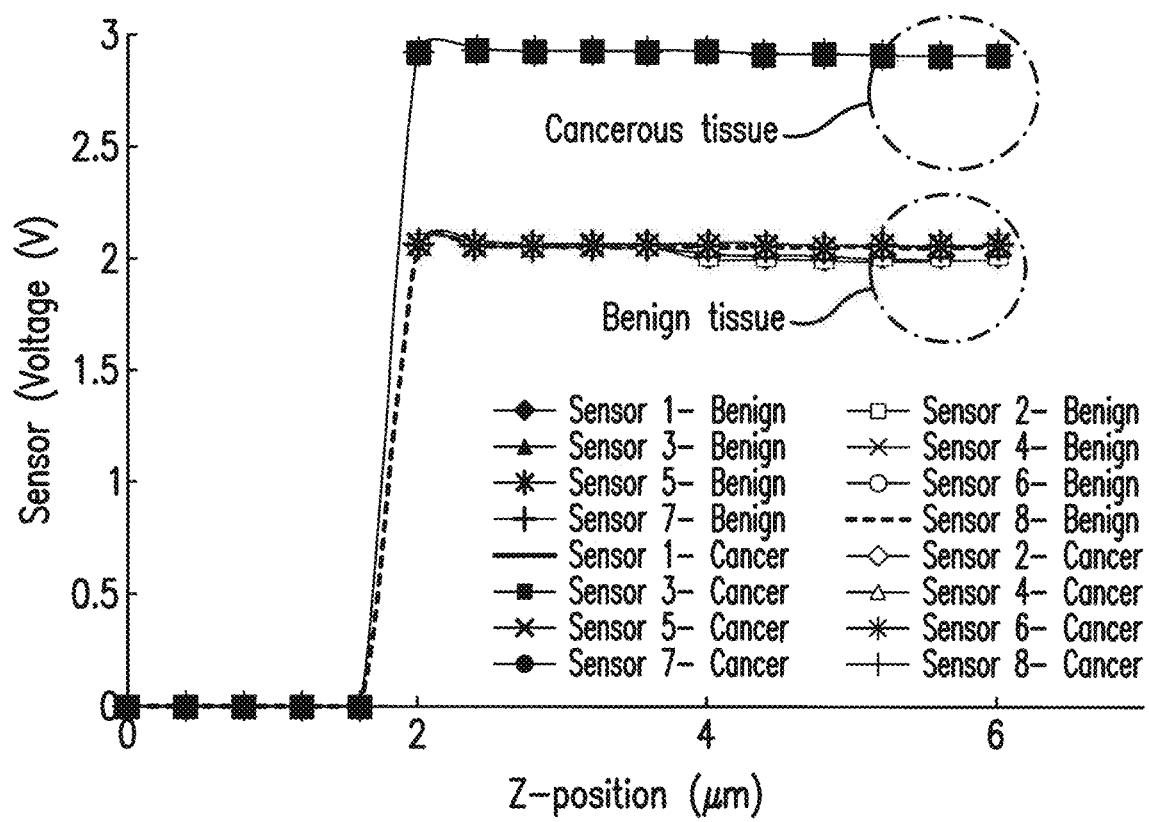
FIG. 22 is a diagram representative of the electrical characterization of tissue samples based on the response of the subject system for benign and cancerous tissue samples.

When the electrode (E1) touches the tissue sample, the current passes through the top electrode (E1) through the breast tissue to the bottom electrode (E2). Depending on the resistance of the breast tissue, the current passing through the tissue would be different and that was reflected in the measured voltage. FIG. 22 shows the voltage values obtained from the sensor when pressed down (about 4 μm) on the tissue core.

From FIG. 22, it was observed that there is a difference in the conductivity of the breast tissue between benign and cancerous tissue cores. It is important to note that a variety of other electrical signals of varying frequency can be passed through the tissue and that the tissue resistance is not the only electrical parameter for characterizing the tissue electrical properties.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A measurement system configured for multi-parameter measurement routine for biological tissue- or cancer-sample characterization, the system comprising:
   a biochip holder module comprising a tissue sample receiving chamber;
   a biochip comprising an integrated array of multi-functional micro-sensors, wherein the array of multi-functional micro-sensors is configured to measure two or more of electrical, mechanical, and thermal properties of a tissue sample, and wherein the biochip is disposed in said biochip holder module;
   a micro-indentation mechanism comprising an indenter, or an array thereof, that is configured to move from an initial position to a sensing position to operatively couple to the tissue sample when the tissue sample is received within said tissue sample receiving chamber, wherein said micro-indentation mechanism is configured to controllably apply a predetermined pressure to the tissue sample by the indenter when the indenter is in the sensing position and sandwiching the tissue sample between said biochip and the indenter to establish a substantially contiguous contact at least between said biochip and the tissue sample during a measurement routine, and wherein, during said measurement routine, said array of multi-functional micro-sensors is used to produce a plurality of multi-parameter measurement signals characterizing the two or more of electrical, mechanical, and thermal properties of the tissue sample; and
   a processor sub-system operatively coupled to said biochip and is programmed to process said plurality of multi-parameter measurement signals for the biological tissue- or cancer-sample characterization.

2. The system of claim 1, wherein said array of multi-functional micro-sensors includes a combination of one or more electrical micro-sensors, one or more mechanical micro-sensors, and one or more temperature micro-sensors, and wherein the combination of the one or more electrical, mechanical, and temperature micro-sensors is used to simultaneously measure the two or more of the electrical, thermal, and mechanical properties of the tissue sample.

3. The system of claim 1, wherein said biochip further includes a micro-heater, wherein the micro-heater is integrated with the biochip, and wherein said micro-indentation mechanism further includes a temperature micro-sensor configured to measure the thermal properties of the tissue sample affected by said micro-heater.

4. The system of claim 2, wherein said biochip includes an integrated one or more mechanical micro-sensors and one or more electrical micro-sensors, the integrated one or more mechanical micro-sensors and one or more electrical micro-sensors comprising:
   a flexible substrate comprising at least one of a compliant piezoelectric material, a compliant piezoresistive material, and a polymer material,
   an array of contact pads formed on said flexible substrate, and
   an array of electrical connectors micro-fabricated on said flexible substrate, wherein a connector of the array of electrical connectors respectively extends in a predetermined manner between a respective contact pad of said array of contact pads and a respective micro-sensor of said array of multi-functional micro-sensors,
   wherein said one or more mechanical micro-sensors include an array of contact-force or contact-pressure sensors formed of a patterned layer comprising the compliant piezoelectric, piezoresistive, polymer material, and
   wherein said one or more electrical micro-sensors include an array of pillars formed from a dielectric material disposed on top of said array of the contact-force or contact-pressure sensors, each of said pillars coated with a metal film on top and along at least one side of the pillar.

5. The system of claim 4, wherein said biochip further includes a metal pad integrated therewith, wherein the metal pad is disposed centrally on one or among more than one pillars of the array of pillars of a given micro-sensor, wherein said metal pad serves as a bottom electrode of at least one of the one or more electrical micro-sensors or sensor elements, wherein said each of said pillars of the given micro-sensor is formed with a bottom thereunder and is in an electrical connection with said metal pad, and
wherein the indenter of said micro-indentation mechanism is fabricated with a top electrode formed thereon, and wherein said bottom and top electrodes are configured to form an electrical connection through the tissue sample when the tissue sample is sandwiched between the indenter of the micro-indentation mechanism and the biochip and in contiguous contact therewith.

6. The system of claim 3, further comprising:
a controller unit, the controller unit being operatively coupled to said processor sub-system,
wherein said micro-indentation mechanism further includes a micro-manipulator in operative coupling to said controller unit and the indenter coupled, at one end thereof, to said micro-manipulator for reciprocative displacement of a second end of said indenter relative to the tissue sample and said biochip,
wherein said top electrode and said temperature micro-sensor are formed at said second end of said indenter,
wherein said micro-manipulator, under control of said controller unit, is configured to controllably apply the predetermined pressure onto the tissue sample and to determine a contact point between said second end of said indenter and the tissue sample.

7. The system of claim 6, wherein said micro-manipulator is configured to displace said indenter, or array thereof, to press the tissue sample onto the tops of one or more of the each of said pillars to transfer the pressure to said array of contact-force or contact-pressure sensors, wherein said array of contact-force or contact-pressure sensors is disposed underneath said array of said pillars, and wherein responsive to the pressure applied thereto, and wherein said array of contact-force or contact-pressure sensors is configured to produce at least one output signal corresponding to an elasticity of the tissue sample.

8. The system of claim 6, wherein, during said measurement routine, said micro-manipulator is configured to displace said top electrode to establish a contiguous contact of said top and bottom electrodes with the tissue sample when the tissue sample is sandwiched between said top and bottom electrodes, and
wherein, during said measurement routine, a current passes between said top and bottom electrodes to produce at least one measurement signal of the plurality of multi-parameter measurement signals, wherein the at least one measurement signal is associated with the electrical properties of the tissue sample, wherein said electrical properties includes at least one of a resistance property and an electrical impedance property.

9. The system of claim 6, wherein said micro-manipulator includes a piezomotor configured to generate at least one of a nano-scale indentation and micro-scale indentation of the tissue sample.

10. The system of claim 6, wherein said biochip holder module includes a holder body configured to house the processor sub-system, wherein the processor sub-system comprises:
a printed circuit board (PCB) module comprising a signal transmission unit configured for transmission of said plurality of multi-parameter measurement signals to the controller unit via a wireless or wire communication channel, wherein said PCB module includes electrical connectors that extend to said biochip through said holder body to be in operative electrical contact with said array of contact pads.

11. The system of claim 10, wherein said top portion of said biochip holder module includes an opening for receiving the tissue sample, wherein said tissue sample receiving chamber is disposed at a top end of said biochip holder module, and in contact with said opening, wherein said tissue sample receiving chamber is disposed at a bottom end of said biochip holder module and in contact with said biochip, and wherein, during said measurement routine, said indenter is brought in alignment with said opening.

12. The system of claim 1, further comprising a base platform configured to support said biochip holder module and said micro-indentation mechanism in a predetermined positional relationship therebetween.

13. The system of claim 1, further including:
a digital display operatively coupled to said biochip to receive and display the data corresponding to said plurality of multi-parameter measurement signals, and
a control unit operatively coupled to said digital display, said biochip, said micro-indentation mechanism, and said processor sub-system, wherein the control unit includes an interface to receive input from a user.

14. The system of claim 1, wherein said processor sub-system communicates with a DAQ unit for conversion of said plurality of multi-parameter measurement signals.

15. The system of claim 12, wherein said portable cancer or pathology diagnostic system is configured as a hand-held device, the system including:
a hand-held module configured with a housing comprising said base platform with said micro-indentation mechanism supported thereon and said biochip holder module removably installed on said base platform,
an on-board power supply integrated with said hand-held module, wherein said hand-held module is operatively coupled to said digital display, said control unit, and said processor sub-system, and
an actuating mechanism for the measurement routine, wherein said digital display and said processor sub-system are integrated with a device selected from a group including said hand-held module, an external mobile device, and combination thereof, and wherein, upon actuation of said measurement routine, said control unit, under control of said processor sub-system, initiates or aborts said measurement routine and subsequent data analysis.

16. The system of claim 1, wherein the measurement system is configured as a portable system for tissue- or cancer-sample diagnostics of meso- or micro-sized tissue or specimen.

17. The system of claim 1, wherein the biochip and integrated array of multi-functional micro-sensors are fabricated as a single micro-electromechanical device.

18. The system of claim 2, wherein said biochip includes an integrated one or more mechanical micro-sensors and one or more electrical micro-sensors, the integrated one or more mechanical micro-sensors and one or more electrical micro-sensors comprising:
a non-compliant substrate comprising at least one of a non-compliant silicon material, a non-compliant piezoelectric material, a non-compliant piezoresistive material, and a non-compliant polymer material;
an array of contact pads formed on said non-compliant substrate, and an array of electrical connectors micro-fabricated on said non-compliant substrate, wherein a connector of the array of electrical connectors respectively extends in a predetermined manner between a respective contact pad of said array of contact pads and a respective micro-sensor of said array of multi-functional micro-sensors;

wherein said one or more mechanical micro-sensors include an array of contact-force or contact-pressure sensors formed of a patterned layer comprising a silicon, piezoelectric, piezoresistive, polymer material, or a combination thereof, and wherein said one or more electrical micro-sensors include an array of pillars formed from a dielectric material atop said array of the contact-force or contact-pressure sensors, each of said pillars coated with a metal film on top and along at least one side of the pillar.

19. The system of claim 1, wherein the measurement system is configured for multi-parameter measurement routine for cancer-sample diagnostics.

20. A method of using the measurement system of claim 1, the method comprising:

moving the indenter of the micro-indentation mechanism from the initial position to the sensing position to operatively couple the tissue sample to said tissue sample receiving chamber and to sandwich the tissue sample between the biochip and the indenter to establish the substantially contiguous contact between said biochip and the tissue sample;

executing said measurement routine to produce the plurality of multi-parameter measurement signals to characterize the two or more of electrical, mechanical, and thermal properties of the tissue sample; and processing said plurality of measurement signals for the biological tissue- or cancer-sample characterization.

* * * * *